US009957541B2

(12) United States Patent
Sunstrom

(10) Patent No.: US 9,957,541 B2

(45) **Date of Patent: *May 1, 2018**

(54) CELL EXPRESSION SYSTEM

(71) Applicant: NeuClone Biologics Pty Ltd, Eveleigh, New South Wales (AU)

(72) Inventor: Noelle Sunstrom, Eveleigh (AU)

(73) Assignee: NeuClone Biologics Pty Ltd, Eveleigh, NSW (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/148,930

(22) Filed: May 6, 2016

(65) Prior Publication Data

US 2016/0244799 A1 Aug. 25, 2016

Related U.S. Application Data

(63) Continuation of application No. 14/773,287, filed as application No. PCT/AU2014/000129 on Feb. 17, 2014, now Pat. No. 9,404,078.

(30) Foreign Application Priority Data

Aug. 3, 2013 (AU) ................................ 2013900804
Aug. 3, 2013 (AU) ................................ 2013900808

(51) Int. Cl.

*C12N 15/67* (2006.01)
*C07K 14/61* (2006.01)
*C12P 21/02* (2006.01)
*C12N 15/85* (2006.01)
*C12N 5/073* (2010.01)
*C12P 21/00* (2006.01)
*C12N 9/06* (2006.01)

(52) U.S. Cl.

CPC .............. *C12P 21/02* (2013.01); *C07K 14/61* (2013.01); *C12N 5/0605* (2013.01); *C12N 15/67* (2013.01); *C12N 15/85* (2013.01); *C12P 21/005* (2013.01); *C07K 2317/14* (2013.01); *C12N 9/003* (2013.01); *C12N 2510/02* (2013.01)

(58) Field of Classification Search

CPC ...... C12P 21/02; C12P 21/005; C12N 5/0605; C12N 15/67; C12N 15/85; C12N 2510/02; C07K 14/61; C07K 2317/14

See application file for complete search history.

(56) References Cited

U.S. PATENT DOCUMENTS 6,340,574 B1 1/2002 Hunt
7,919,270 B2 4/2011 Kunaparaju
9,404,078 B2 8/2016 Sunstrom
2011/0250640 A1 10/2011 Otto
2016/0017277 A1 1/2016 Sunstrom

FOREIGN PATENT DOCUMENTS

| | | |
|---|---|---|
| EP | 0584788 | 3/1994 |
| JP | 2011525800 | 9/2011 |
| KR | 20070043902 | 4/2007 |
| KR | 772031 | 10/2007 |
| WO | WO 1997005240 | 2/1997 |
| WO | WO 2002046430 | 6/2002 |
| WO | WO 2003106658 | 12/2003 |
| WO | WO 2003046162 | 6/2006 |
| WO | 2009156511 | 12/2009 |

OTHER PUBLICATIONS

Moulin et al., Hormone and Metabolic Research, (2003) vol. 35, No. 7, pp. 396-401 (Year: 2003).*

Lee et al., Gene, (2001) vol. 270, No. 1-2, pp. 121-129 (Year: 2001).*

Möller et al., J. Biol. Chem., 267 (1992), pp. 23403-23408 (Year: 1992).*

Huang et al. (2004) "Process Development for a Recombinant Chinese Hamster Ovary (CHO) Cell Line Utilizing a Metal Induced and Amplified Metallothionein Expression System" Biotech and Bioengineering 88(4):437-450.

Palma-Nicolas et al. (2005) "Production of recombinant human placental variant growth hormone in Pichia pastoris" Biotech. Letters 27:1695-1700.

(Continued)

*Primary Examiner* — Daniel C Gamett

(74) *Attorney, Agent, or Firm* — Michael B. Rubin; Bozicevic, Field & Francis LLP

(57) ABSTRACT

An expression system for expressing a protein comprising: a eukaryotic host cell carrying a dihydrofolate reductase (DHFR) deficiency; and an expression vector, the expression vector encoding the human growth hormone gene; a expression vector, the expression vector comprising: a eukaryotic selectable marker including a minimal SV 40 early promoter driving expression of a sequence encoding dihydrofolate reductase for complementing the DHFR deficiency in the host cell; a prokaryotic selectable marker conveying Ampicillin resistance to a prokaryotic host cell; a prokaryotic Origin of Replication; a plurality of multiple cloning sites (MCS); and at least one protein expression module comprising: a Simian Vacuolating Virus 40 (SV40) early promoter, inclusive of its 72 bp enhancer repeats; and a rabbit β-globin intron sequence being separable from a SV40 p A sequence by a first multiple cloning site, for receiving a coding sequence and expressing a desired protein therefrom.

9 Claims, 11 Drawing Sheets

(56) References Cited

OTHER PUBLICATIONS

Suzuki et al. (2000) "In Vivo Expression of Human Growth Hormone by Genetically Modified Murine Bone Marrow Stromal Cells and its Effect on the Cells In Vitro" Cell Transplantation 9:319-327.
Yamashita et al. (2000) "The Effect of Growth Hormone on the Proliferation of Human Th Cell Clones" Life Sciences 66(20):1929-1935.
Madrid Olga et al. (2002) "Growth hormone protects against radiotherapy-induced cell death"; European Journal of Endocrinology 147(4); pp. 535-541.
Van Dyk Derek D. et al. (2003) "Identification of cellular changes associated with increased production of human growth hormone in a recombinant Chinese hamster ovary cell line"; Proteomics 3(2); pp. 147-156.
Wurm Florian M. (2004) "Production of recombinant protein therapeutics in cultivated mammalian cells"; Nat Biotechnol. 22(11); pp. 1393-1398.
Zhang, Jinyou et al. (2010) "Mammalian Cell Culture for Biopharmaceutical Production"; Manual of Industrial Microbiology and Biotechnology, Third Edition, American Society of Microbiology; pp. 157-178.
Barnes and Sato (1980) "Methods for Growth of Cultured Cells in Serum-Free Medium" *Anal. Biochem.* 102:255-270.
Bulleid et al. (2000) "Recombinant expression systems for the production of collagen" *Biochem. Soc. Transactions* 28(4):350-353.
Cacciatore, J.J., et al., "Gene amplification and vector engineering to achieve rapid and high-level therapeutic protein production using the Dhfr-based CHO cell selection system", Biotechnology Advances, 2010, 28:673-681.
Choi et al. (1999) "Molecular and functional characterization of chicken IL-15" *Development & Comparative Immunology* 23:165-177.
Durocher et al. (2002) "High-level and high-throughput recombinant protein production by transient transfection of suspension-growing human 293-EBNA1 cells" *Nucleic Acids Res.* 30(2):e9.
Dyck et al. (2003) "Making recombinant proteins in animals—different systems, different applications" *Trends in Biotechnol.* 21(9):394-399.
Fischer et al. (1999) "Towards molecular fanning in the future: moving from diagnostic protein and antibody production in microbes to plants" *Biotechnol. Appl. Biochem.* 30:101-108.
Garber (2001) "Biotech industry faces new bottleneck" *Nature Biotechnol.* 19:184-185.
Girard et al. (2002) "100-liter transient transfection" *Cytotechnol.* 38:15-21.
Ho, Steven CL, et al., "Generation of monoclonal antibody-producing mammalian cell lines", 2013, Pharm. Bioprocess., 1(1):71-87.
Hunt, S.M.N., et al., "Chinese hamster ovary cells produce sufficient recombinant insulin-like growth factor I to support growth in serum-free medium", Cytotechnology, 1997, 24:55-64.
Kuhlmann, M & Covic, A., "The protein science of biosimilars", Nephrology Dialysis Transplantation, 2006, 21(Suppl 5):v4-v8.
Kunaparaju et al. (2005) "Epi-CHO, an Episomal Expression System for Recombinant Protein Production in CHO Cells" *Biotechnol. and Bioengineering* 91(6):670-677.
Meissner et al. (2001) "Transient Gene Expression: Recombinant Protein Production with Suspension-Adapted HEK293-EBNA Cells" *Biotechnol. and Bioengineering* 75(2):197-203.
Mendiaz et al. (1986) "A Defined Medium for and the Effect of Insulin on the Growth, Amino Acid Transport, and Morphology of Chinese Hamster Ovary Cells, CHO-K1 (CCL 61) and the Isolation of Insulin "Independent" Mutants" *In Vitro Cellular & Developmental Biology* 22(2):66-74.
Morishita et al. (1998) "Conditioned Medium From HepG2 Cells Transfected With Human Apolipoprotein(a) Gene Stimulates Growth of Human Vascular Smooth Muscle Cells: Effects of Overexpression of Human Apolipoprotein(a) Gene" *Hypertension* 32:215-222.
Morton and Potter (2000) "Comparison of *Escherichia coli, Saccharomyces cerevisiae, Pichia pastoris, Spodoptera frugiperda*, and COS7 Cells for Recombinant Gene Expression" *Molecular Biotechnol.* 16:193-202.
Mukhina et al. (2004) "Phenotypic conversion of human mammary carcinoma cells by autocrine human growth hormone" *PNAS* 101(42):15166-15171.
Pak et al. (1996) "Super-CHO—A cell line capable of autocrine growth under fully defined protein-free conditions" *Cytotechnology* 22:139-146.
Pandey et al. (2008) "Autocrine Human Growth Hormone Stimulates Oncogenicity of Endometrial Carcinoma Cells" *Endocrinology* 149(8):3909-3919.
Pavlou and Belsey (2005) "The therapeutic antibodies market to 2008" *European J. of Pharmaceutics and Biopharmaceutics* 59:389-396.
Sunstrom, N.A., et al., "Regulated autocrine growth of CHO cells", Cytotechnology, 2000, 34:39-46.
Verma et al. (1998) "Antibody engineering: Comparison of bacterial, yeast, insect and mammalian expression systems" *J. of Immunological Methods* 216:165-181.
Walsh (2006) "Biopharmaceutical benchmarks 2006" *Nature Biotechnology* 24(7):769-776.
Werner, RG (1998) "Appropriate mammalian expression systems for biopharmaceuticals." *Arzneimittelforschung* 48(8):870-880.
Zhu, J., "Mammalian cell protein expression for biopharmaceutical production", Biotechnology Advances, 2012, 30:1158-1170.

* cited by examiner

CELL EXPRESSION SYSTEM

TECHNICAL FIELD

The present invention relates to expression systems, in particular the invention relates to expression systems for the production of biological therapeutics.

BACKGROUND

Expression systems for the production of biological therapeutics or biopharmaceuticals, such as recombinant proteins, generally consist of a nucleic acid vector construct encoding the desired recombinant therapeutic and a chosen host cell. The vector is introduced into the host cell and the endogenous cell machinery is utilised for the production of the desired therapeutic i.e. the desired recombinant protein. The intricacies in establishing an efficient and reliable expression system for the production of approvable biological therapeutics are manifold. However, well-established expression systems may provide cost-effective alternatives for the production of pharmaceutical products otherwise difficult to obtain.

Efficiency of the system itself depends on a large variety of factors including the design of the vector and the choice of host cell. The strategic combination of regulatory elements, selection markers and stability elements within the vector sequence have to balance simple manipulation and application of the vector with high yield production of the desired biological therapeutic. Determining a cell's suitability to act as host cell in such an expression system is primarily governed by the need to maximise compatibility between the endogenous cell machinery and the regulatory elements present in the vector, while keeping potential adventitious contaminants in the final product minimal. Further, availability, cost and acceptability for regulatory approval of any therapeutic produced by the system, have to be considered.

Nucleic acid vectors used in expression systems comprise plasmids, cosmids, Yeast Artificial Chromosomes (YACs), Bacterial Artificial Chromosomes (BACs), retroviral. adenoviral and lentiviral vectors. These vectors differ in many characteristics, such as their capacity to accommodate different sized nucleic acid inserts. their most efficient introduction method into the host cell and specifically in their utilisation of the endogenous cell machineries of different types of host cells to ensure sufficient expression of the desired protein.

Regulatory elements commonly present in such expression vectors influence transcription. translation as well as protein synthesis of selection markers and of sequences encoding the desired biological therapeutic. Such regulatory elements include, but are not limited to, promoters, terminators, modifiers, insulators, spacers, regulatory protein binding sites, introns, inducers, etc.

Known promoters include constitutively active promoters such as the thymidine kinase (TK) promoter, the actin promoter, the glyceraldehyde 3-phosphate dehydrogenase (GAPDH) promoter, the simian vacuolating virus 40 (SV40) early promoter, the cyclin T1 promoter, the RNA polymerase III U3 promoter, the cyclophillin promoter, the cytomegalovirus (CMV) promoter, the *Autographa californica* nuclear polyhedrosis virus (AcNPV) P10 promoter and the β3-galactosyltransferase 5 (β3GAL-T5) promoter.

Known promoters also include inducible promoters such as the heat shock protein 70 (HSP70) promoter (stress induced), the heat shock protein 90 (HSP90) promoter (stress induced), the alcoholdehydrogenase I (alcA) promoter (alcohol induced), the activating copper-metallothionein expression (ACE1) promoter (metal induced), the small subunit of ribulose-1,5-bisphophate-carboxylase (SSU1) promoter (light induced), the hypoxia induced factor 1α (hif1α) promoter (hypoxia induced), the inducer of meiosis 2 (IME2) promoter (starvation induced), the glucocorticoid receptor (hormone induced), the estrogen receptor (hormone induced) and the ecdysone receptor (hormone induced).

Further, cell type/tissue specific promoters, such as the nkx2.5 promoter (heart cells), the islet 1 promoter (pancreatic cells), the MyoD promoter (muscle cells), the cluster of differentiation 2 (CD2) promoter (T-cells) and the collagen II promoter (cartilage), are known to change their level of activity in response to cell type specific stimuli or to progression through developmental stages.

Known terminator elements, such as the RNA Polymerase II terminator, the small nucleolar RNA 13 (snR13) terminator, the bovine growth hormone (BGH) terminator, the simian virus 40 (SV 40) terminator and the thymidine kinase (TK) terminator, may provide suitable polyadenylation signals.

Known modifier and insulator elements include the tetracycline operator/receptor (tetO/tetR) system, the upstream activating sequence of the galactose dependent GAL4 transcription factor (GAL4 UAS), the adenovirus early region B1 TATA box, binding sites for the herpes simplex virus (HSV) regulatory protein VP16, the 5'HS4 chicken β-globin insulator, the paternally expressed gene 3 (Peg3) insulator and the sea urchin arylsulfatase (ARS) gene insulator.

While many attempts have been made to establish efficient and reliable expression systems for the production of approvable biological therapeutics, problems relating to low yield and adventitious contamination of the produced biopharmaceuticals remain. Choosing the most effective combination of suitable regulatory elements from the plethora of options, such that the system conveys stability and the highest degree of compatibility with the endogenous host cell machinery, poses a major challenge in the field.

Obtaining regulatory approval for a biopharmaceutical product poses a further challenge. Regulatory approval involves determination of the safety and efficacy of the pharmaceutical product prior to marketing. The process of gaining regulatory approval for innovator drugs is very time consuming and expensive. However, once approved, these drugs may be very profitable. particularly when they are marketed under exclusivity rights such as patent protection.

The profitability of innovator drug's market may provide a substantial incentive to exploit this market once patent rights have expired. Following patent expiry, innovator drugs can be marketed as generic drugs or biosimilars for drugs produced by recombinant DNA technology. Generic versions of blockbuster biopharmaceuticals near patent expiry include Epogen (erythropoietin, EPO) and Neupogen (granulocyte colony stimulating factor, G-CSF). The approval of a follow-on version of Pfizer's Genotropin (recombinant human growth hormone) seems to indicate a change in a landscape where previously, biopharmaceuticals enjoyed immunity from competition even after expiration of their patent protection. At present, there are over 80 generic versions of biopharmaceuticals in development (Datamonitor 2010).

Biosimilars ideally are bioequivalents of the innovator drugs and, as such, the path to regulatory approval for biosimilars is in theory less arduous than for the original innovator drug as the clinical data establishing safety and efficacy have been carried out.

Approval of generic biopharmaceuticals is dependent on comparable dosage form, strength, route of administration, quality. performance characteristics and intended use compared with approved biopharmaceuticals (that is, the reference listed drugs). For example, under the United States Food and Drug Administration (FDA), approval for a generic drug involves an "Abbreviated New Drug Application" (ANDA) which generally does not include pre-clinical and clinical data to establish safety and effectiveness. Approval also involves a bioequivalence review, which establishes that the proposed generic drug is bioequivalent to the reference-listed drug. This bioequivalency is based upon a demonstration that the rate and extent of absorption of the active ingredient in the generic drug fall within the scope of the parameter of the reference listed drug.

Importantly, there is a chemistry/microbiology review process that provides an assurance that the generic drug will be manufactured in a reproducible manner under controlled conditions to ensure that the drug will perform in a safe and acceptable manner.

Although guidelines for the approval of biosimilar drugs exist, there is uncertainty in regard to the practicalities of regulatory approval of biosimilars. Much of the uncertainty is driven by the lack of a clear practical and detailed regulatory pathway for the approval of such drugs and the scientific debate over product comparability and interchangeability. The uncertainties resulting from the manufacture of biosimilar drugs under conditions different than those used by the innovator suggest that it may be impossible to develop a true "generic" version of a biotechnology drug. Indeed, regulatory authorities in Europe and the US have shunned the use of the term "biogeneric", preferring the nomenclature "biosimilar" and "follow-on biologicals".

Many quality concerns for expression system-derived biopharmaceuticals have originated from the presence of adventitious contaminants or from the properties of the host cells used to prepare the product. Several of these products have also had quality concerns regarding the expression vector of the system. It is well established that cell properties and events linked to cell culture can affect resultant product quality and safety. Effective quality control of recombinant products requires appropriate controls on all aspects of handling the cell and cell culture. This is particularly relevant to the development of biosimilars.

Previously, Chinese Hamster Ovary (CHO) cells were modified and engineered to produce insulin. However these CHO cells were unable to express biological active insulin and thus the patents associated with this type or method of CHO cell modification were not commercial exploited. Fully functional insulin was not produced in CHO cells due to cryptic splicing of the insulin gene message by the translational machinery In the CHO cell.

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

SUMMARY

Means for Solving the Problem

A first aspect of the present invention may relates to novel expression systems and methods of employing an expression system according to the invention that may, in certain embodiments, increase the yield and decrease the cost of manufacture.

This invention relates to methods of production of recombinant biosimilars, bio-pharmaceuticals and other desirable proteins, polypeptides and peptides using mammalian cell cultures. In particular, the methods of the invention involve the use of specially bioengineered mammalian cell lines for the production of complex proteins in low cost media. These cell lines have the acquired ability for autonomous growth in cheap. reproducible, fully-defined protein-free medium, with the cells expressing and secreting its growth factor requirements.

Accordingly, in a first aspect, the present invention provides an expression system for expressing a protein comprising:

a eukaryotic host cell carrying a dihydrofolate reductase (DHFR) deficiency an expression vector, the expression vector encoding the human growth hormone gene;

an expression vector, the expression vector comprising:

a eukaryotic selectable marker downstream of for expression of a sequence encoding dihydrofolate reductase for complementing the DHFR deficiency in the host cell;

a prokaryotic selectable marker conveying Ampicillin resistance to a prokaryotic host cell;

a prokaryotic Origin of Replication a plurality of multiple cloning sites (MCS); and at least one protein expression module comprising:

a Simian Vacuolating Virus 40 (SV40) early promoter, inclusive of its 72 bp enhancer repeats; and a rabbit β-globin intron sequence being separable from a SV40 polyadenylation sequence by a first multiple cloning site, for receiving a coding sequence and expressing a desired protein therefrom.

Preferably, the expression system further comprises a second protein expression module, the second protein expression module including: a Cyotomegalovirus promoter being separable from a SV40 polyadenylation sequence by a second multiple cloning site for co-expression of at least two proteins from the expression modules.

Preferably, the protein is the subject of a request for regulatory approval and wherein the host cell is subjected to a plurality of predetermined manipulations such that the host cell expresses said protein; and wherein information is recorded on each manipulation and each manipulation is carried out in a manner which prevents contact of the host cell with a contaminating agent; and wherein the information is used to generate a history record of the host cell for inclusion in a submission to a regulatory agency involved in assessing the safety and efficacy of drugs thereby expediting regulatory approval of the protein.

The predetermined manipulations preferably comprise:

(i) ligating the coding sequence encoding the desired protein into the expression vector to produce a recombinant vector;

(ii) introducing the recombinant vector into the host cell; and (iii) culturing the host cell under conditions such that the protein is expressed by the host cell.

Preferably the recombinant vector is at least in part incorporated into the genome of the host cell. Step (iii) includes growing the host cell in a medium that contains no animal or plant derived proteins or peptides and no undefined hydolysates or lysates thereby reducing contact of the host cell with a contaminating agent.

In a particularly preferred embodiment, the host cell is a Chinese Hamster Ovary (CHO) DG44 cell.

In certain preferred embodiments, the host CHO DG44 expresses a growth hormone. In certain preferred embodiment the growth hormone is human growth hormone. In certain preferred embodiments, the protein may be a biosimilar drug.

In a second aspect, the present invention provides a method of managing the development of a protein expressed by the expression system according to the first aspect wherein the protein is the subject of a request for regulatory approval, the method comprising the steps of:

a. subjecting the host cell to a plurality of predetermined manipulations such that the cell expresses the protein;
b. recording information on each manipulation wherein each manipulation is carried out in a manner which prevents contact of the host cell with a contaminating agent;
c. using the information to generate a history record of the host cell for inclusion in a submission to a regulatory agency involved in assessing the safety and efficacy of drugs; and
d. including the history record in the submission to the regulatory agency for regulatory approval of the product.

In a third aspect, the present invention provides a method of expediting regulatory approval of a protein expressed by the expression system according to the first aspect the method comprising:

b. subjecting the host cell to a plurality of predetermined manipulations such that the host cell expresses the product;
c. recording information on each manipulation wherein each manipulation is carried out in a manner which prevents contact of the host cell with a contaminating agent;
d. using the information to generate a history record of the host cell for inclusion in a submission to a regulatory agency involved in assessing the safety and efficacy of drugs; and
e. including the history record in the submission to the regulatory agency for regulatory approval of the protein.

Preferably, step (a) of the methods according to the second and third aspect comprises (i) ligating the coding sequence encoding the desired protein into the expression vector to produce a recombinant vector;
(ii) introducing the recombinant vector into the host cell; and
(iii) culturing the host cell under conditions such that the protein is expressed by the host cell.

The recombinant vector is preferably at least in part incorporated into the genome of the host cell.

Preferably, step (iii) of the methods according to the second and third aspect includes growing the host cell in a medium that contains no animal or plant derived proteins or peptides and no undefined hydrolysates or lysates thereby reducing contact of the host cell with a contaminating agent.

In a particularly preferred embodiment of the methods according to the second and third aspect, the protein is a biosimilar drug.

Another aspect of the present invention may also provide a method for producing a desired recombinant protein, polypeptide or peptide comprising the step of: culturing a mammalian host cell in culture medium, wherein said host cell includes:

(i) at least one introduced DNA sequence encoding a protein, polypeptide and/or peptide factor(s) required for growth of the host cell in said culture medium. expressibly linked to a constitutive promoter (e.g. CMV and SV40 promoters) The invention thereby enables the use of low cost, protein/serum-free medium by utilising a host cell which is able to produce the protein, polypeptide and/or peptide growth factor(s) required for its growth in such medium. The culture medium used in the method of the invention is, therefore, preferably serum-free or otherwise free of protein, polypeptide and/or peptide growth factor(s) necessary for the growth of the particular host cell type. However, methods wherein the culture medium includes one or more of the required growth factor(s) and the host cell itself expresses one or more of the same and/or other required growth factor(s), is also to be regarded as falling within the scope of the invention.

The mammalian host cell may be any of those commonly used in the art for expressing recombinant proteins, polypeptides or peptides. For example, the host cell may be a Chinese Hamster Ovary (CHO) cell such as CHO-K1, CHO-DG44 DHFR- and CHO-S. These include both adherent and suspension cell lines. Also other cell lines described within the embodiments of the present invention may also be used or preferred.

The introduced DNA sequence(s) may be present on plasmids or otherwise integrated into the host cell chromosomes (e.g. by homologous recombination).

The DNA sequence(s) encoding the protein, polypeptide and/or peptide factor(s) required for growth of the host cell, may be selected from DNA sequences encoding human Growth Hormone (hGH), modified hGH and other growth factors and mixtures thereof. Where the host cell is CHO it is preferable that the host cell includes DNA sequences encoding human Growth Hormone (hGH).

In the context of the present invention, the words "comprise", "comprising" and the like are to be construed in their inclusive, as opposed to their exclusive, sense, that is in the sense of "including, but not limited to".

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

Figure 1A:
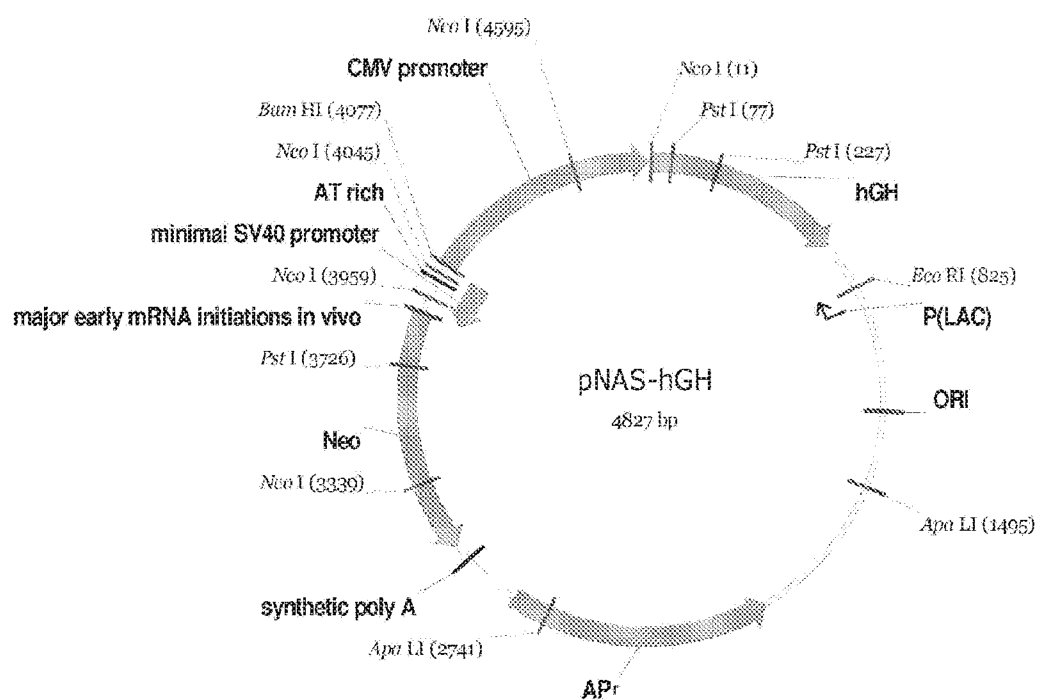
FIG. 1A is a plasmid vector map entitled "pNAS-hGH" for the high level expression human growth hormone (hGH) inserted within a pNAS vector with use with NeuCHO cell line.

This specification also includes the following genetic sequence information relating to expression vectors:

Sequence No. 1 depicts the preferred coding sequence for the expression vector pMAB HC;

Sequence No. 2 depicts the preferred coding sequence for the expression vector pMAB LC(ires-dhfr);

Sequence No. 3 depicts the preferred coding sequence for the expression vector pNAS-hGH;

Sequence No. 4 depicts the preferred coding sequence for the expression vector pNeu;

Sequence No. 5 depicts the preferred coding sequence for the expression vector pNeu-IRES-DHFR;

Sequence No. 6 depicts the preferred coding sequence for the expression vector pNeuMAB;

Sequence No. 7 depicts the preferred coding sequence for the expression vector pNeuMAB-IRES-DHFR (CMV);

Sequence 8 depicts the preferred coding sequence for the expression vector pNeuMAB-IRES-DHFR;

Please note that in this specification Sequence No. is same and the equivalent term to SEQ ID NO.

DESCRIPTION OF THE INVENTION

Preferred embodiments of the invention will now be described with reference to the accompanying drawings and non-limiting examples.

It has been found that events during the culture of a cell may contribute significantly to the assessment of the risks associated with the use of that particular cell for production of proteins and more particularly proteins for therapeutic use.

Diligent records of all manipulations including the history of a cell throughout development, extending to the parental cell line from which it was derived. may contribute to the quality and safety of the final product.

In one scenario, such information may be important for gaining regulatory approval of protein therapeutics expressed from a cell. In particular, biosimilars present unique issues. These issues include demonstrating that immunogenicity of the biosimilar has not been altered with respect to the reference listed drug, as well as ensuring that there are no undetected differences in the product that may potentially impact the safety and efficacy of the drug. Resolving such issues would be problematic without conducting extensive clinical trials. As such, it is likely that any application for a biosimilar would be required to demonstrate that there are no clinically meaningful differences in safety, purity and potency between the biosimilar and the reference listed drug. Moreover, an application for a biosimilar would need to provide evidence that the biosimilar has "profound similarity" (as it is impractical to demonstrate identical biological products) and that the biosimilar will produce the same clinical result as the reference listed drug in any given patient.

In order to gain regulatory approval, traditional generic manufacturers are required to demonstrate their drug is chemically identical to the referenced listed drug and exhibit the same properties in the human body as the original drug. In regard to biosimilars. it was previously not possible to readily demonstrate that a second-source biologic drug is unequivocally identical to an innovator drug due to the complexities of the synthesis of the drugs in potentially disparate biological systems. As such, biosimilars may exhibit slightly different properties to the original drugs that may necessitate abbreviated clinical trials in order to gain regulatory approval.

In the context of the present invention, the term "contaminating agent" refers to any agent that can potentially compromise regulatory approval of a product by a regulatory agency. Such agents may include but are not limited to adventitious agents such as viruses, bacteria, fungi and *mycoplasma* or proteins there from.

As used herein the term "cell expressed product" refers to any product produced by the cell, including but not limited to proteins. peptides, glycoproteins, carbohydrates, lipids, glycolipids and nucleic acids.

The term "regulatory approval" in so far as it relates to a product defined in the context of this specification, refers to approval from a regulatory authority which permits marketing of the product.

The term "safety and effectiveness studies" refers to any studies conducted on a product that assess the safety and efficacy of that product for human and/or animal administration.

The term "clinical trials" refers to studies involving either animal or humans designed assess the safety and/or efficacy of a product for a therapeutic application.

The term "abbreviated safety effectiveness studies and/or abbreviated clinical trials" refers to studies carried out on a drug which does not involve complete phase I, II and III clinical trials. Such studies may include a bioequivalence review and a chemistry/microbiology review as defined by the US Food and Drug Administration (FDA).

The term "biosimilar drug" and "biosimilar" refer to a bioequivalent pharmaceutical of a drug in which patent protection has expired and where the previously protected drug has regulatory approval. In particular, this includes products prepared in cell culture by recombinant DNA technology. The term "biosimilar drug" and "biosimilar" as used herein is equivalent to the terms "follow-on biologicals" or "biosimilars".

The term "protein" refers to a "complete" protein as well as fragments. derivatives or homologs or chimeras thereof comprising one or more amino acid additions, deletions or substitutions, but which substantially retain the biological activity of the complete protein.

The embodiments of the present invention will now be described by reference to the following non-limiting examples.

EXAMPLE 1

Construction of pNeu and pNAS Vectors for High Level Expression of Recombinant Therapeutic Protein The vector pNeu was designed for high-level expression of single chain peptides for the production of therapeutic proteins. The vector facilitates the insertion DNA sequences into a convenient multiple cloning site for expression in CHO cells. See Table 1 and FIG. 1A for a description of the vector and its component features.

The 5026 bp vector encodes essential coding and regulatory sequences for the efficient expression of the recombinant gene as well as essential sequences for the selection and propagation of the plasmid in bacteria. It was designed for chemical synthesis and is void of nonessential and redundant sequences that are common components in commercial expression vectors. This allows for ease of genomic insertion with less likelihood of deletion of sequences during plasmid propagation resulting in loss of expression. The multiple cloning site encodes a minimum of two unique restriction sites for rapid gene cloning.

EXAMPLE 2

Synthesis and Cloning of Human Growth Hormone (hGH) cDNA into pNAS

The amino acid sequence encoding for hGH was subjected to bioinformatic analysis through proprietary third party software by GENEART AG, Regensburg Germany. Codon options were utilized to maximize expression by improving mRNA maintenance and the exploitation of available tRNA pools in CHO cells. RNA and codon optimization was performed on the coding sequences. The gene was analysed with respect to splice site recognition, mRNA stability, presence of ribosomal entry sites, mRNA secondary structures, self-homology for the purpose of increasing gene expression in CHO cells. The hGH gene was cloned into pNAS using AgeI and EcoRV restriction sites using methods well known in the art.

EXAMPLE 3

Construction of pNeuMAB Vector for Expression of Recombinant Monoclonal Antibody The pNeuMAB vector was designed for the cloning and expression of recombinant monoclonal antibodies. The DNA encoding heavy and light chains are configured in the vector as two distinct and tandem transcription units. See Table 1 and FIG. 1B for a description of the vector and its component features.

Synthesis of cDNA Encoding Heavy Chain and Light Chain of an Antibody—Infliximab The amino acid sequence encoding the heavy chain (HC) and light chain (LC) of the monoclonal antibody, Infliximab were subjected to bioinformatic analysis through proprietary third party software by GENEART AG, Regensburg Germany. Codon options were utilized to maximize expression by improving mRNA maintenance and the exploitation of available tRNA pools in CHO cells. RNA and codon optimization was performed on the coding sequences. The genes were analysed with respect to splice site recognition, mRNA stability, presence of ribosomal entry sites, mRNA secondary structures, self-homology for the purpose of increasing gene expression in CHO cells.

Cloning Gene Encoding Heavy Chain of Infliximab

The synthetic gene encoding for the heavy chain of Infliximab was assembled from synthetic oligonucleotides and/or PCR products. The fragment was cloned into pGA14 (ampR) using AscI and PacI restriction sites. The plasmid DNA was purified (Pure Yield™ Plasmid Midiprep, Promega) from transformed bacteria and concentration determined by UV spectroscopy. The final construct was verified by sequencing. The sequence congruence within the used restriction sites was 100%. The synthetic cDNA sequence encoding heavy chain of Infliximab was designed to incorporate unique restriction sites Age I and Eco RV at the 5' and 3' ends respectively for directional cloning into the first multiple cloning site of NeuClone's antibody expression vector, pNeuMAB digested with the same restriction sites.

Cloning Gene Encoding Light Chain of Infliximab

The synthetic gene encoding the light chain of Infliximab was assembled from synthetic oligonucleotides and/or PCR products. The fragment was cloned into pGA18 (ampR) using AscI and PacI restriction sites. The plasmid DNA was purified (Pure Yield™ Plasmid Midiprep, Promega) from transformed bacteria and concentration determined by UV spectroscopy. The final construct was verified by sequencing. The sequence congruence within the used restriction sites was 100%. The synthetic cDNA sequence encoding light chain of Infliximab incorporates the unique restriction sites Sal I and Mlu I at the 5' and 3' ends respectively for directional cloning into the second multiple cloning site of NeuClone's antibody expression vector, pNeuMAB digested with the same restriction sites.

Generation of NeuCHO

Transfection of DG44 Cells with pNAS-hGH

One of the preferred methods by which the expression vector encoding human growth hormone into the host CHO DG44 cell line and the status of the rDNA within the host (copy number. etc.) is as follows. Briefly, a total of 1.5×10e7 cells were transfected with 1.8 ug of linearized plasmid DNA together with 15 ul of FreeStyle MAX Reagent (Invitrogen) in a volume of 30 ml. The transfected cell cultures were incubated at 37 C. 8% CO2 on an orbital shaker platform. At 48 hours post transfection the cells were cultured in hypoxanthne- and thymidine-deficient, medium supplemented with Gentamycin at a final concentration of 500 ug/ml for selection of uptake of plasmid DNA. Clones were selected by limiting dilution cloning. Several single clones arising from a single cell were expanded and cell lines were characterised for production of human growth hormone. Resulting clones were examined for growth properties in comparison to the standard CHO DG44 cell line.

Transfection of NeuCHO with pNeuMAB Encoding Infliximab Genes

Linearized plasmid pNeuMAB DNA encoding Infliximab genes was used to transfect NeuCHO cell cultures At 48 hours post transfection the cells were cultured into hypoxanthne- and thymidine-deficient, medium to select for cells expressing the DHFR gene. A stable cell population was then subjected to subsequent stepwise increasing methotrexate (MTX) concentration (50-, 100-, 200-, 400-, 800 nM, 1 uM) in order to amplify template DNA copy number and gene expression. Clones were selected by limiting dilution cloning. Clones with high level expression of infliximab protein were scaled up for protein production.

EXAMPLE 4

Cell Banking

A critical part of quality control involves the full characterization of cells. The cell banks are examined for adventitious agents (viral, bacterial, fungal and mycoplasmal). Documentation describing the type of banking system used, the size of the cell bank(s) the container (vials. ampoules and closure system used, the methods used for preparation of the cell bank(s) including the cryoprotectants and media used, and the conditions employed for cryopreservation and storage are provides.

The procedures used to avoid microbial contamination and cross-contamination by other cell types present in the laboratory, and the procedures that allow the cell bank containers to be traced are all made available. This includes a description of the documentation system as well as that of a labelling system which can withstand the process of preservation, storage, and recovery from storage without loss of labelling information on the container.

It is essential that production is based on a well-defined master and working cell bank system. During the establishment of the banks no other cell lines are handled simultaneously in the same laboratory suite or by the same persons. The origin, form, storage, use and expected duration at the anticipated rate of use are described in full for all cell banks.

The following table identifies some of the components and features of the various expression vectors using with either CHO DG44 or NeuCHO cell lines. The data has been divided into three tables for purposes of presentation in this patent specification.

TABLE 1

| Feature | pNeu | pNeu-IRES-DHFR | pNAS | pNeuMAB |
|---|---|---|---|---|
| Multiple cloning site | One multiple cloning site for insertion of expression unit coding for single chain protein | One multiple cloning site for insertion of expression unit coding for single chain protein | One multiple cloning site for insertion of expression unit coding for single chain protein | Two multiple cloning sites for insertion of expression units coding for heavy and light chains of a monoclonal antibody |
| Strong promoter/enhancer combination | The SV40 virus early promoter/enhancer | The SV40 virus early promoter/enhancer | The CMV early promoter/enhancer drives expression of each transcription unit | The SV40 virus early promoter/enhancer drives expression of the first and 2nd transcription unit |
| Intron/intervening sequence | The intron sequence II from rabbit beta globin gene is located downstream of the promoter providing for increased expression and mRNA stability of the transcription unit | The intron sequence II from rabbit beta globin gene is located downstream of the promoter providing for increased expression and mRNA stability of the transcription unit | | The intron sequence II from rabbit beta globin gene is located downstream of the promoter providing for increased expression and mRNA stability of the first transcription unit |
| Internal Ribosome Entry Site (IRES) | | For the expression of DHFR gene downstream of 2$^{nd}$ transcription unit ensuring high level expression of 2$^{nd}$ cistron in cells growing in the presence of methotrexate | | |
| Polyadenylation signal | A strong polyadenylation signal from S40 virus for efficient expression of recombinant gene. | A strong polyadenylation signal from S40 virus for efficient expression of recombinant gene. | A strong polyadenylation signal from S40 virus for efficient expression of recombinant gene | A strong polyadenylation signal from S40 virus is for efficient expression of each recombinant gene |
| DHFR gene | Auxotrophic selection in HT negative media eliminates the need to maintain selection | Auxotrophic selection in HT negative media eliminates the need to maintain selection | | Auxotrophic selection in HT negative media eliminates the need to maintain selection pressure using |

TABLE 1-continued

| Feature | pNeu | pNeu-IRES-DHFR | pNAS | pNeuMAB |
|---|---|---|---|---|
| | pressure using antibiotics. Amplification of gene copy number is accomplished by the addition of methotrexate to the culture media. The murine DHFR gene is driven by a minimal SV40 early promoter lacking the enhancer sequence. | pressure using antibiotics. Amplification of gene copy number is accomplished by the addition of methotrexate to the culture media. The murine DHFR gene is driven by a minimal SV40 early promoter lacking the enhancer sequence. | | antibiotics. Amplification of gene copy number is accomplished by the addition of methotrexate to the culture media. The murine DHFR gene is driven by a minimal SV40 early promoter lacking the enhancer sequence |
| Ampicillin resistance gene | For propagation of plasmid in bacteria | For propagation of plasmid in bacteria | For propagation of plasmid in bacteria | For propagation of plasmid in bacteria |
| Neomycin gene | | | For selection in mammalian cells | |

TABLE 2

| Features | pNeuMAB-IRES-DHFR | pNeuMAB-IRES-DHFR (CMV) | pMAB-LC (ires-dhfr) |
|---|---|---|---|
| Multiple cloning site | Two multiple cloning sites for insertion of expression units coding for heavy and light chains of a monoclonal antibody | Two multiple cloning sites for insertion of expression units coding for heavy and light chains of a monoclonal antibody | One multiple cloning site for insertion of Light chain gene |
| Strong promote/enhancer combination | The SV40 virus early promoter/enhancer drives expression of the first and 2nd genes | The SV40 virus early promoter/enhancer drives expression of the first gene and the CMV promoter drives expression of the $2^{nd}$ gene. | The SV40 virus early promoter/enhancer drives expression of LC gene |
| Intron/intervening sequence | The intron sequence II from rabbit beta globin gene is located downstream of the promoter providing for increased expression and mRNA stability of the transcription unit | The intron sequence II from rabbit beta globin gene is located downstream of the promoter providing for increased expression and mRNA stability of the transcription unit | The intron sequence II from rabbit beta globin gene is located downstream of the promoter providing for increased expression and mRNA stability of the transcription unit |
| Intenal Ribosome Entry Site (IRES) | For the expression of DHFR gene downstream of $2^{nd}$ transcription unit ensuring high level expression of $2^{nd}$ cistron in cells growing in the presence of methotrexate | For the expression of DHFR gene downstream of $2^{nd}$ transcription unit ensuring high level expression of $2^{nd}$ cistron in cells growing in the presence of methotrexate | For the expression of DHFR gene downstream of $2^{nd}$ transcription unit ensuring high level expression of $2^{nd}$ cistron in cells growing in the presence of methotrexate |

TABLE 2-continued

| Features | pNeuMAB-IRES-DHFR | pNeuMAB-IRES-DHFR (CMV) | pMAB-LC (ires-dhfr) |
|---|---|---|---|
| Polyadenylation signal | A strong polyadenylation signal from S40 virus for efficient expression of recombinant gene. | A strong polyadenylation signal from S40 virus for efficient expression of recombinant gene. | A strong polyadenylation signal from S40 virus for efficient expression of recombinant gene. |
| DHFR gene | Auxotrophic selection in HT negative media eliminates the need to maintain selection pressure using antibiotics. Amplification of gene copy number is accomplished by the addition of methotrexate to the culture media. The murine DHFR gene is driven by a minimal SV40 early promoter lacking the enhancer sequence. | Auxotrophic selection in HT negative media eliminates the need to maintain selection pressure using antibiotics. Amplification of gene copy number is accomplished by the addition of methotrexate to the culture media. The murine DHFR gene is driven by a minimal SV40 early promoter lacking the enhancer sequence. | Auxotrophic selection in HT negative media eliminates the need to maintain selection pressure using antibiotics. Amplification of gene copy number is accomplished by the addition of methotrexate to the culture media. The murine DHFR gene is driven by a minimal SV40 early promoter lacking the enhancer sequence. |
| Ampicillin resistance gene | For propagation of plasmid in bacteria | For propagation of plasmid in bacteria | For propagation of plasmid in bacteria |
| Neomycin gene | | | |

TABLE 3

| Features | pMAB-HC |
|---|---|
| Multiple cloning site | One multiple cloning site for insertion of Heavy chain gene. Vector is similar to pNAS |
| Strong promoter/enhancer combination | The CMV early promoter/enhancer drives expression of heavy chain gene |
| Intron/intervening sequence | |
| Intenal Ribosome Entry Site (IRES) | |
| Polyadenylation signal | A strong polyadenylation signal from S40 virus for efficient expression of recombinant gene. |
| DHFR gene | |
| Ampicillin resistance gene | |
| Neomycin gene | For selection in mammalian cells |

FIG. 1 A-H depicts a series of expression vector map relevant to expression using CHO DG44 cell lines or NeuCHO cell lines.

More specifically, FIG. 1A depicts an expression vector pNAS including hGH coding sequence for use in constructing the NeuCHO Cell Line from CHO DG44. Preferably, NeuCHO cell line is produced by the inclusion of the vector shown in FIG. 1A within a CHO-DG44 cell line. The genetic sequence for this expression vector has been submitted along with this application and is designated SEQ. ID No. 1.

It is noted that CHO DG44 cell line includes a relatively and fragile cell line which inherently has issues and problems in regard to long term viability, cell density and population stability.

In this preferred embodiment, the addition of hGH to the cell culture vector may lead to increases in cell density or production that were previously not realizable using previous techniques and sequences. Previously, growth factors such as IGF-1 and insulin were used to supplement CHO cells (such as DG44). However these previous methods lead to disappointing results in terms of cell viability and/or survival. In the present embodiments, the addition of hGH coding sequences to CHO cells allows for the excretions by the CHO-DG44 cells of hGH. This expression and secretion of hGH into the cell media leads to increase in cell survival of CHO cells.

Further the expression of hGH may also improve the robustness of the NeuCHO cell line as compared to other CHO cell lines.

More specifically, the addition of hGH expressing sequences to CHO-DG44 cells gave rise to a new cell line, NeuCHO cell line. The NeuCHO cell line may include any of the expression vectors described and shown in respect to FIG. 1 A-H.

The NeuCho cell line, deposited under the provisions of the Budapest Treaty with the Cell Bank Australia located at 214 Hawkesbury Rd, Westmead, NSW, 2145, Australia as of 4 Feb. 2013 and assigned accession no. CBA20130024, as is particularly suitable for use in pharmaceutical manufacture as described within the present application.

Preferably, the CHO-DG44 cell line was transfected with the pNAS-hGH vector to produce the NeuCHO cell line. Possible transfection methods include: standard methods described in the scientific literature including: calcium phosphate precipitation, PEI, Electroporation and lipofaction. It is generally noted that previous teachings in the field have often argued that it is preferred to deliver higher relative levels of DNA to cells by transfection to get better results. However, transfection methods delivering more DNA into the cell do not generate more stable or high producing cell lines, as the cell lines may become less stable and less robust.

Figure 1B:
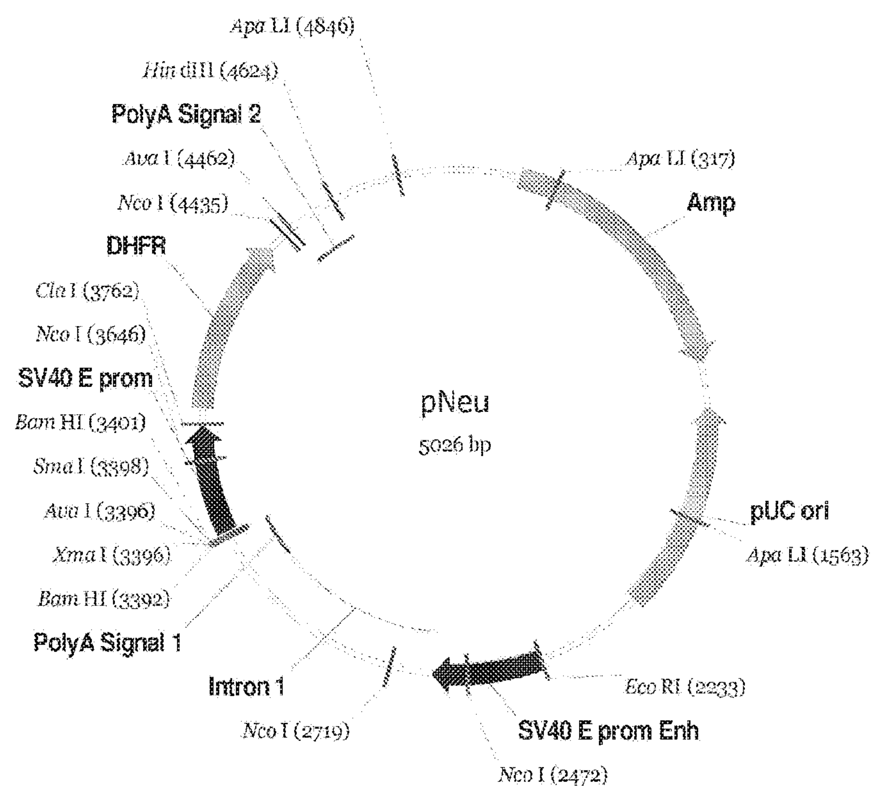
FIG. 1B is an expression vector map entitled "pNeu" used for the high level expression of a single chain protein in CHO DG44 cells.

FIG. 1B depicts an expression vector used for the expression of a single chain protein in CHO DG44 cells. Preferably, the recombinant gene expression may be driven by the SV40 early promoter/enhancer within the vector. The genetic sequence for this expression vector has been submitted along with this application and is designated SEQ. ID No. 2.

Figure 1C:
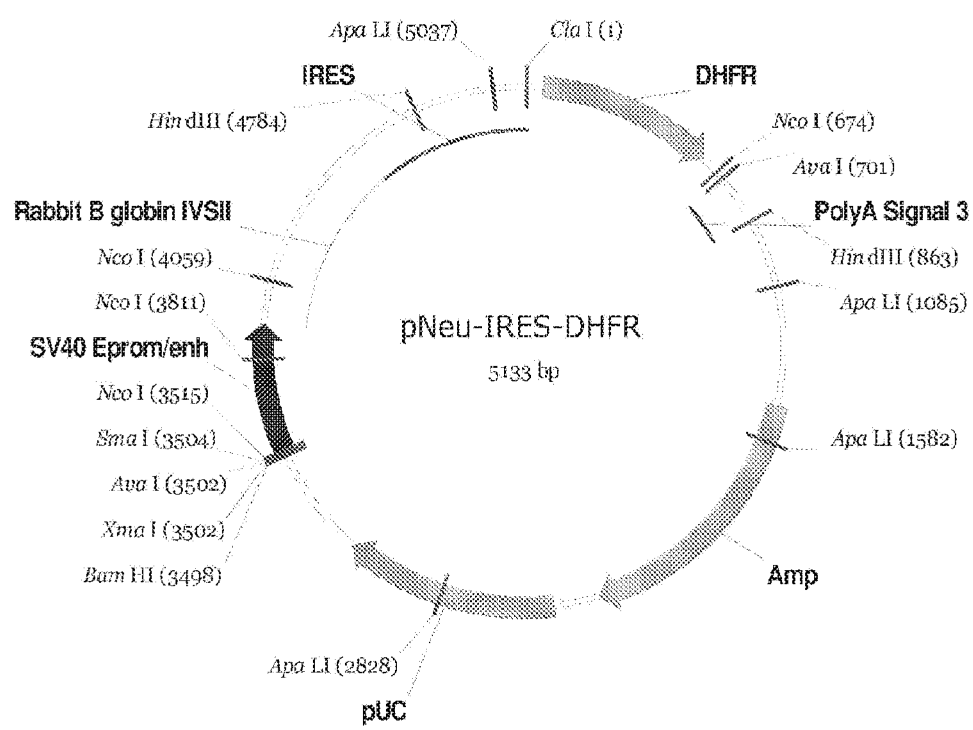
FIG. 1C is an expression vector map entitled "pNeu-IRES-DHFR" used for the high level expression of a single chain protein in CHO DG44 cells. A dicistronic expression cassette with recombinant gene in $1^{st}$ cistron followed by DHFR gene in $2^{nd}$ cistron.

FIG. 1C depicts an expression vector used for the expression of a single chain protein in CHO DG44 cells. Preferably, a dicistronic expression cassette with a recombinant gene in the $1^{st}$ cistron followed by a DHFR gene in the $2^{nd}$ cistron is described in this example. The gene expression in this vector is preferably driven by SV40 early promoter or enhancer. The genetic sequence for this expression vector has been submitted along with this application and is designated SEQ. ID No. 3.

Figure 1D:
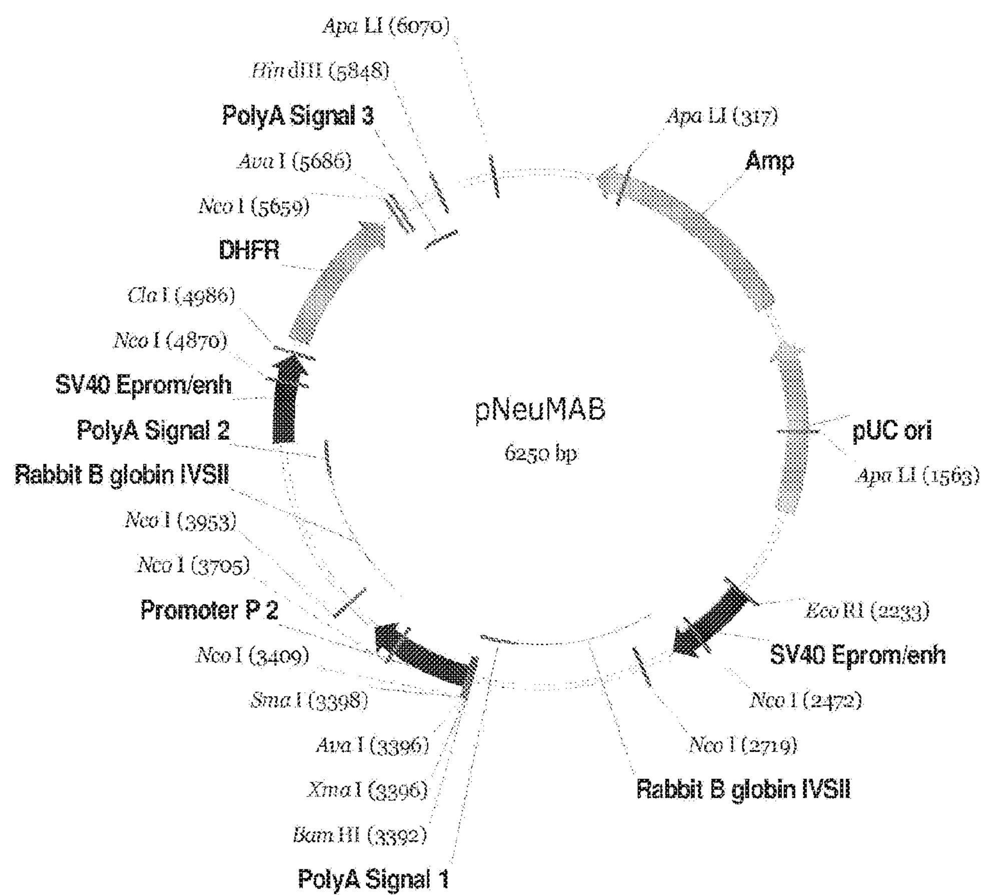
FIG. 1D is an expression vector map entitled "pNeuMAB" used for the high level expression of heavy and light antibody chains and/or recombinant monoclonal antibodies.

FIG. 1D depicts a pNeuMAB, which is a dual expression vector containing two cloning cassettes to insert heavy and light chain genes into a single vector. This expression vector has two gene expression cassettes for the insertion of multiple recombinant genes. Each cassette includes an SV40 early promoter and downstream poly A sequence. Each gene is driven by driven SV40 promoter without an enhancer sequence. This expression vector is suitable for expression of light and heavy chains expression of the antibodies. The genetic sequence for this expression vector has been submitted along with this application and is designated SEQ. ID No. 4.

Figure 1E:
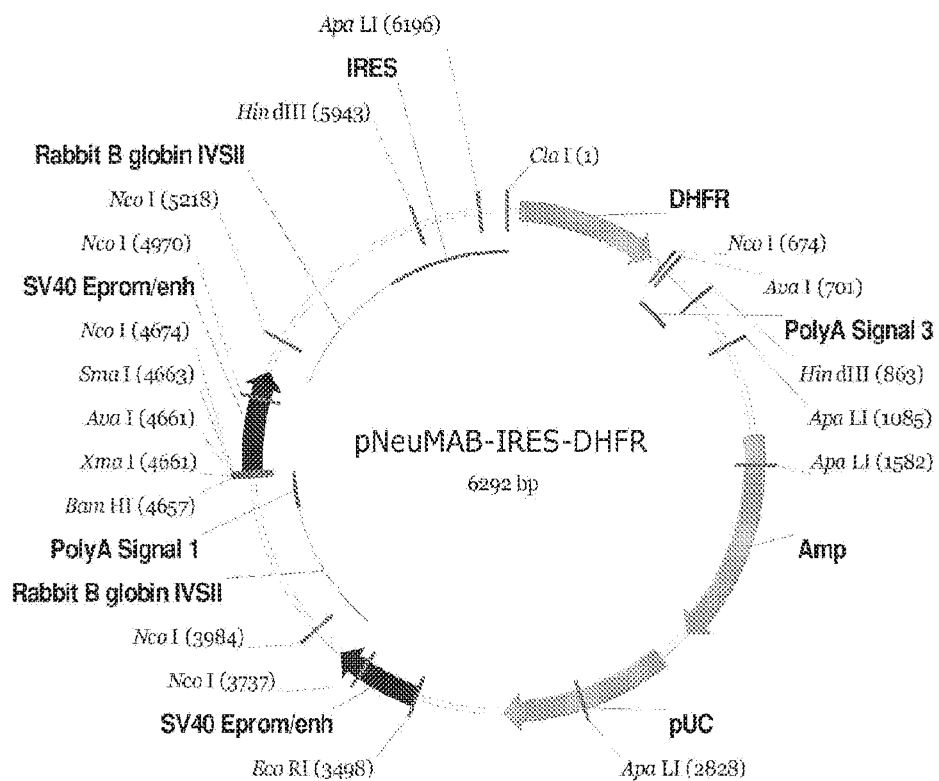
FIG. 1E is an expression vector map entitled "pNeuMAB-IRES-DHFR" used for the high level expression of heavy and light antibody chains.

FIG. 1E depicts a further expression vector, pNeuMAB-IRES-DHFR, for high level expression of heavy and light chains of a recombinant monoclonal antibody on a single vector driven one SV40 promoter and enhancer. This expression vector may be used for the expression of light and heavy antibody chains. This expression vector generally includes two gene expression cassettes for insertion of recombinant genes. Each cassette consists of SV40 early promoter/enhancer and downstream poly A sequence. Heavy chain and light chain are inserted in 1st and 2nd cassettes respectively. The 2nd cassette is dicistronic having light chain followed by DHFR downstream of IRES. The genetic sequence for this expression vector has been submitted along with this application and is designated SEQ. ID No. 5.

Figure 1F:
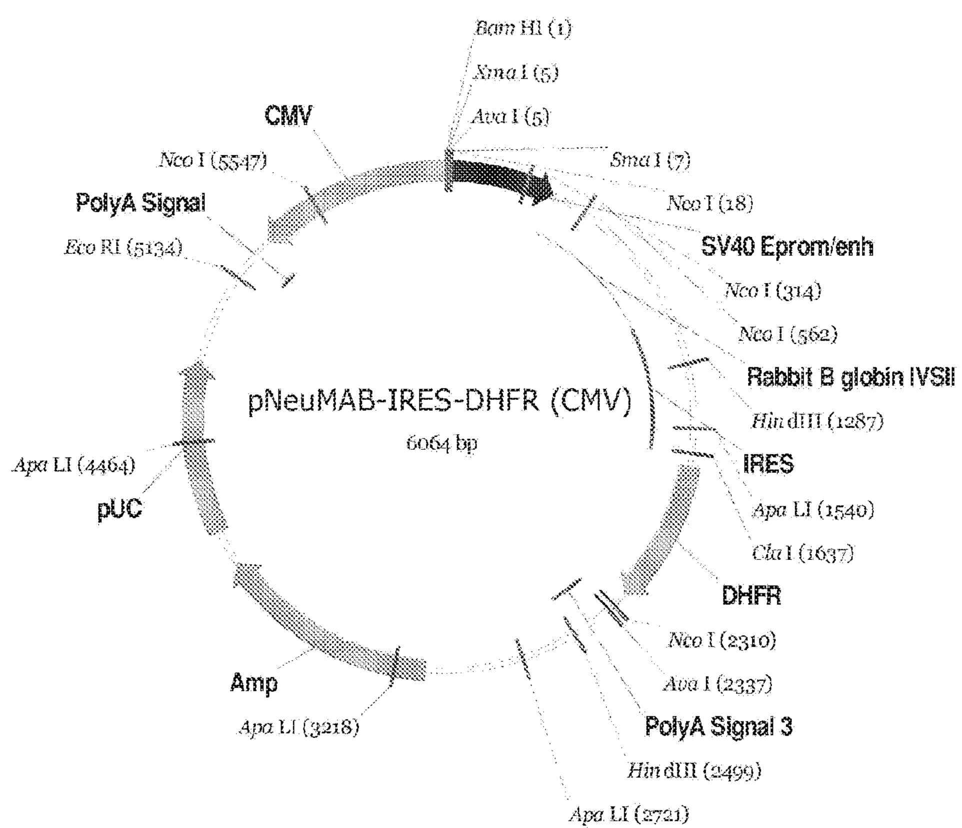
FIG. 1F is an expression vector map entitled "pNeuMAB-IRES-DHFR (CMV)" used for the high level expression of heavy and light antibody chains.

FIG. 1F depicts a further expression vector, pNeuMAB-IRES-DHFR-(CMV), for high level expression of heavy and light chains of recombinant monoclonal antibody on a single vector driven by CMV and SV40 promoters of heavy and light chains of antibodies respectively. The DHFR gene is driven by IRES downstream of light gene; for the expression of heavy and light chains of antibody in opposite orientations with respect to each other. Heavy chain is driven by CMV promoter whereas light chain is driven by SV40 promoter/enhancer. Light chain and DHFR gene have a dicistronic configuration with DHFR downstream of IRES. The genetic sequence for this expression vector has been submitted along with this application and is designated SEQ. ID No. 6.

Figure 1G:
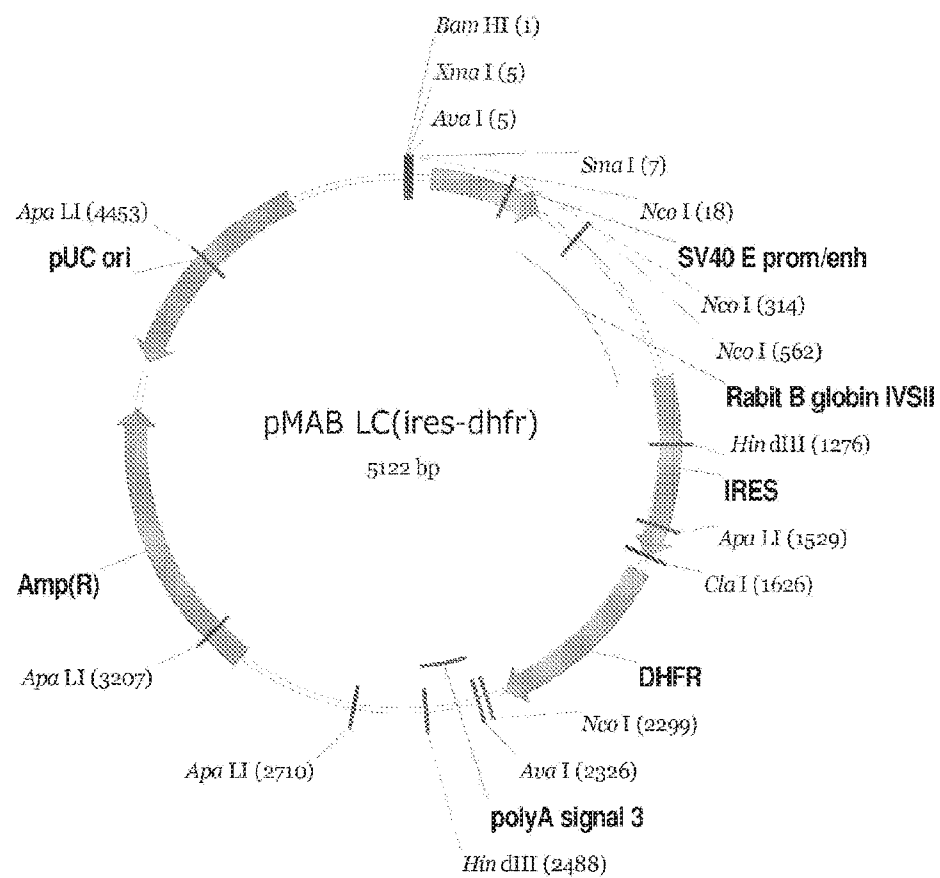
FIG. 1G is a single chain expression vector map entitled "pMAB LC (IRES-DHFR)" used for expression of light chains (LC)

FIG. 1G depicts a further expression vector, pMAB-LC (ires-dhfr), for expression of only light chains (LC) of antibodies. A discistronic cassette for cloning LC in 1st cistron and DHFR in 2nd cassette downstream of IRES. The vector is used in co-transfection with pMAB HC, which is the expression vector shown in FIG. 1H. The genetic sequence for this expression vector has been submitted along with this application and is designated SEQ. ID No. 7.

Figure 1H:
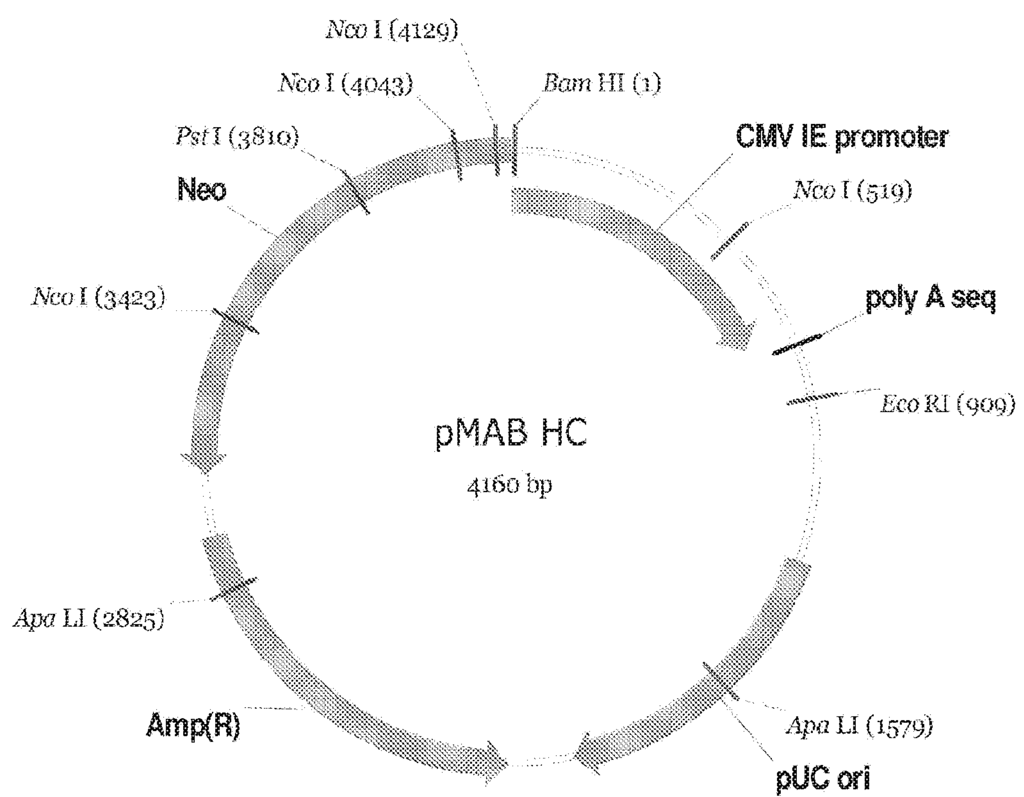
FIG. 1H is a single chain expression vector map entitled "pMAB HC" used for expression of heavy chains (HC)

FIG. 1H depicts a further expression vector, pMAB-HC, for expression of only heavy chain (HC) of antibodies. Both pMAB-LC and pMAb-HC are co-transfected for expression of complete antibody. The genetic sequence for this expression vector has been submitted along with this application and is designated SEQ. ID No. 8.

Figure 2:
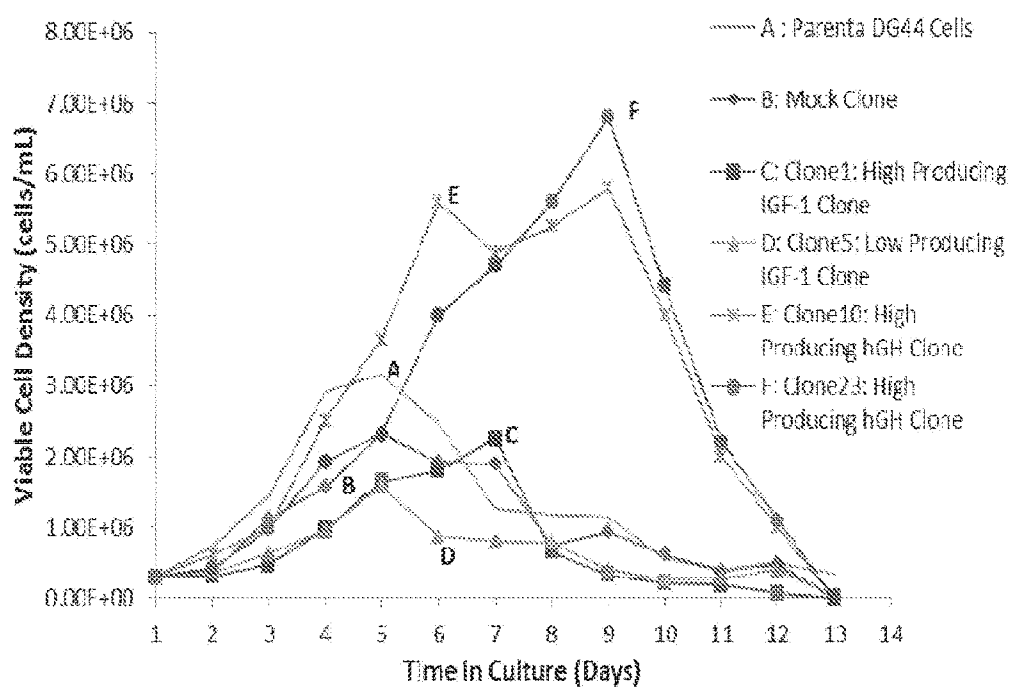
FIG. 2. depicts a growth chart demonstrating viable cell density plotted against time in respect of various cultures and cells used. Growth of DG44 Cell Lines expressing hGH compared to the Parental DG44 Cell Line and a DG44 Cell Line expressing the IGF-1 gene.

A further graph is shown in FIG. 2. The graph of FIG. 2 represents the: Growth of DG44 Cell Lines expressing IGF-1 or hGH compared to the Parental DG44 Cell Line and a Mock Cell Line. A control (mock) cell line is derived from the Parental Cell Line which has been stably transfected with a DNA plasmid containing the selection marker but without the Gene Of Interest (GOI).

The preferred NeuCHO Cell Line demonstrates superior growth advantage compared to the original Parental DG44 Cell Line. In this example, the growth of NeuCHO cells demonstrates higher viable cell densities to that of a DG44 Cell Line expressing the IGF-1 gene.

This graph shows that when DG44 cells express human Growth Hormone, (Line Graphs E and F), the cells have a very high Maximum Viable Cell Density (up to 425%) compared to the untransfected DG44 Parental Cell Line, the Mock transfected Cell Line, and DG44 Cell Lines expressing high or Low IGF-1 protein.

The NeuCHO Cell Line has an Integral Cell Density of up to $3.67\times10^7$ cell/day/mL, which is 230% that of the Parental DG44 Cell Line, $1.57\times10^7$ cell/day/mL.

Also in FIG. 2. the Viable Cell Density is plotted on the Y-axis in cells/mL. and the number of days in culture is plotted on the X-axis. Six line graphs are shown in the figure, namely line graph A, B, C, D, E and F.

Line A represents the growth pattern of a parental DG44 cell line that is not transfected with DNA.

Line B represents the growth pattern of a parental DG44 cell line that was transfected with a DNA plasmid containing the selection marker but without the Gene Of Interest (GOI).

Line C represents the growth pattern of a parental DG44 cell line that was stably transfected with a DNA plasmid containing both the selection marker and the Gene Of Interest (GOI). The GOI here is Insulin-like growth factor 1 (IGF-1).

Line D represents the growth pattern of a parental DG44 cell line that was stably transfected with a DNA plasmid containing both the selection marker and the Gene Of Interest (GOI). The GOI here is Insulin-like growth factor 1 (IGF-1).

Line E represents the growth pattern of a parental DG44 cell line that was stably transfected with a DNA plasmid containing both the selection marker and the Gene Of Interest (GOI). The GOI here is human Growth Hormone (hGH).

Line F represents the growth pattern of a parental DG44 cell line that was stably transfected with a DNA plasmid containing both the selection marker and the Gene Of Interest (GOI). The preferred GOI in this example is human Growth Hormone (hGH).

Figure 3:
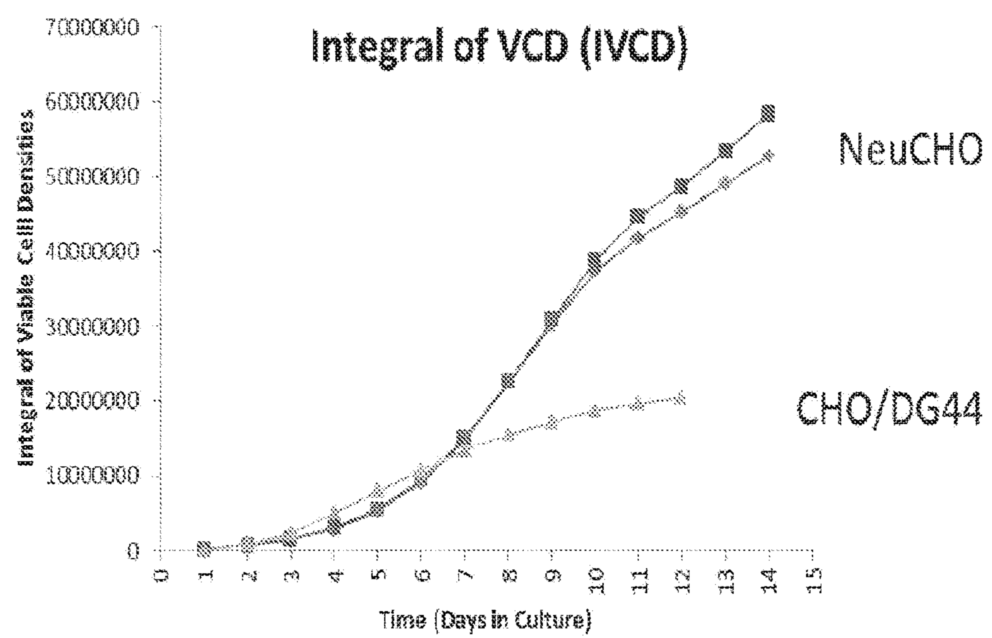
FIG. 3. depicts a graph comparing the integral of viable cell densities against time for various preferred organisms and culture.
Figure 4:
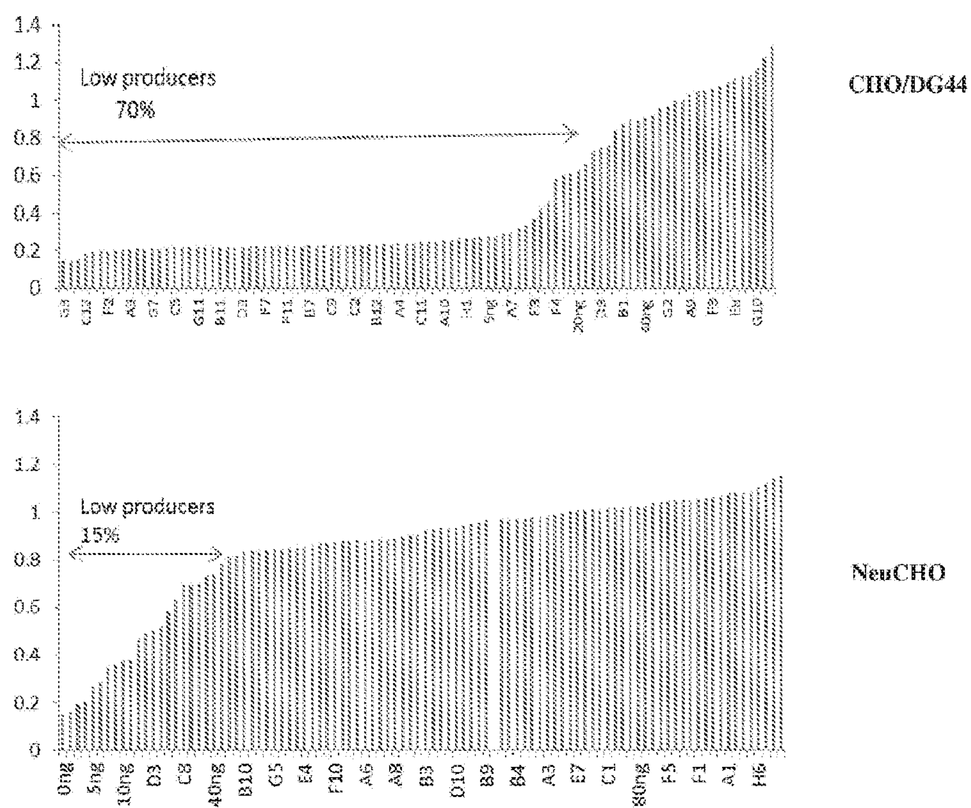
FIG. 4. depicts a comparison chart showing the relative expression levels of proteins from either CHO DG44 cells or NeuCHO cell lines.

In FIG. 3, a further graph is depicted comparing the integral of viable cell densities (IVCD) of NeuCHO with the standard CHO DG44 cells. This figure demonstrates the difference in the Integral of Viable Cell Densities achieved with the parent cell line NeuCHO compared to parental CHO.

The NeuCHO cell line is superior in growth capabilities and this translates into a more efficient production process which can minimize costs by having higher productions rates, fewer production runs, thus lower productions costs, lower Cost of Goods (COGS).

Growth and productivity of NeuCHO cell line expressing a recombinant mAB.

The preferred NeuCHO cell line demonstrates high titre of mAB x compared to traditional CHO expression system.

FIG. 5 demonstrates in graphical form that NeuCHO cells may have greater stable transfection efficiency than CHO cells (such CHO DG44 cells). Cells (NeuCHO and CHO) were transfected with DNA encoding mAB 'x' prior to selection and single cell cloning from a stable pool. The data is shown in FIG. 5 and demonstrates that stable transfection of NeuCHO cells results in a greater number of clones with high productivity than that of standard CHO cells. The graph shows the levels of various protein expressed in relative quantities at a given time.

NeuCHO cells have an integral of viable cell density that is about 230% greater than CHO DG44 cell lines. CHO DG44 cell lines expressing insulin like growth factor 1 (IGF-1) do not demonstrate the ability to grow to high cell densities as NeuCHO cell lines may generally achieved. NeuCHO cells have a generally greater transfection efficiency than CHO DG44 cells. The survival rate of transfected NeuCHO cells is generally greater then transfected CHO DG44 cells. Additionally, transfection of NeuCHO cells may result in a greater number of clones with a higher productivity than that of standard CHO DG44 cells.

Preferably, the expression system and vectors described herein may be able to allow or facilitate CHO cells such NeuCHO or CHO DG44 cells to produce desired proteins suitable for pharmaceutical preparation including, but not limited to: Infliximab tumour necrosis factor (referred to as Remicab™); Adalimumab tumour necrosis factor (referred to as Humira™); Etanercept tumour necrosis factor (referred to as Enbrel™); Rituximnab CD20 (referred to as Rituxan™ & MabThera™); Bevacizumab vascular endothelial growth factor (referred to as Avastin™) Trastuzumab HER2 (referred to as Herceptin™); Ranibizumab vascular endothelial growth factor (referred to as Lucentis™); Cetuximab epidermal growth factor receptor (referred as Erbitux™); Erythropoietin α; Interferon α-Pegylated interferon alfa-2a; Interferon α-Pegylated interferon alfa-2b and hGH.

NeuCHO cells when used as feeder layer may also increase efficiency of single cell cloning. NeuCHO cells were seeded in single wells of microtitre plates prior to single cell cloning of a stable transfected pool. Secretion of human growth hormone secreted from NeuCHO cells results in an increased survival rate of single cells following Limiting Dilution Cloning.

Although the invention has been described with reference to specific examples, it will be appreciated by those skilled in the art that the invention may be embodied in many other forms. in keeping with the broad principles and the spirit of the invention described herein.

The present invention and the described preferred embodiments specifically include at least one feature that is industrial applicable.

The claims defining the invention are as follows:

1. A method for producing a desired recombinant polypeptide comprising culturing a mammalian host cell expressing a desired recombinant polypeptide in a cell culture media comprising a human Growth Hormone (hGH) or modified hGH, wherein the hGH or modified hGH is added to the cell culture media and enhances survival and/or cell density and/or cell viability of the mammalian host cell expressing the desired recombinant polypeptide.

2. The method according to claim 1, wherein the mammalian host cell is a CHO cell.

3. The method according to claim 2, wherein the CHO cell is selected from the group consisting of: a CHO-K1, a CHO-DG44 and a CHO-S cell.

4. The method according to claim 2, wherein the CHO cell has a dihydrofolate reductase (DHFR) deficiency.

5. The method according to claim 1, wherein culturing is performed in a suspension culture.

6. The method according to claim 1, wherein culturing is performed in an adherent culture.

7. The method according to claim 1, wherein the desired recombinant polypeptide is a biosimilar of a recombinant protein.

8. The method according to claim 7, wherein the recombinant protein is selected from the group consisting of: Infliximab, Adalimumab, Etanercept, Rituximab, Bevacizumab, Trastuzumab, Ranibizumab, Cetuximab, Erythropoietin alpha, Interferon alpha, Interferon alpha 2a and Interferon alpha 2b.

9. The method according to claim 1, wherein the addition of the hGH or modified hGH to the cell culture media increases cell density and viability of the host mammalian cell compared to a mammalian cell of the same cell type as the host mammalian cell supplemented with insulin-like growth factor 1 (IGF-1).

* * * * *

SEQUENCE LISTING

```
<160> NUMBER OF SEQ ID NOS: 8

<210> SEQ ID NO 1
<211> LENGTH: 4183
<212> TYPE: DNA
<213> ORGANISM: Artificial Sequence
<220> FEATURE:
<223> OTHER INFORMATION: Synthetic oligonucleotide

<400> SEQUENCE: 1

ccggtctagt taactagcac cgatatcaat gaatgcaatt gttgttgtta acttgtttat     60

tgcagcttat aatggttaca aataaagcaa tagcatcaca aatttcacaa ataaagcatt    120

tttttcactg cattctagtt gtggtttgtc caaactcatc aatgtatctt atcatgtctg    180

aattcgtaat catggtcata gctgtttcct gtgtgaaatt gttatccgct cacaattcca    240

cacaacatac gagccggaag cataaagtgt aaagcctggg gtgcctaatg agtgagctaa    300

ctcacattaa ttgcgttgcg ctcactgccc gctttccagt cgggaaacct gtcgtgccag    360

ctgcattaat gaatcggcca acgcgcgggg agaggcggtt tgcgtattgg gcgctcttcc    420

gcttcctcgc tcactgactc gctgcgctcg gtcgttcggc tgcggcgagc ggtatcagct    480

cactcaaagg cggtaatacg gttatccaca gaatcagggg ataacgcagg aaagaacatg    540

tgagcaaaag gccagcaaaa ggccaggaac cgtaaaaagg ccgcgttgct ggcgtttttc    600

cataggctcc gcccccctga cgagcatcac aaaaatcgac gctcaagtca gaggtggcga    660

aacccgacag gactataaag ataccaggcg tttccccctg gaagctccct cgtgcgctct    720

cctgttccga ccctgccgct taccggatac ctgtccgcct ttctcccttc gggaagcgtg    780

gcgctttctc atagctcacg ctgtaggtat ctcagttcgg tgtaggtcgt tcgctccaag    840

ctgggctgtg tgcacgaacc ccccgttcag cccgaccgct gcgccttatc cggtaactat    900

cgtcttgagt ccaacccggt aagacacgac ttatcgccac tggcagcagc cactggtaac    960

aggattagca gagcgaggta tgtaggcggt gctacagagt tcttgaagtg gtggcctaac   1020
```

```
tacggctaca ctagaaggac agtatttggt atctgcgctc tgctgaagcc agttaccttc   1080
ggaaaaagag ttggtagctc ttgatccggc aaacaaacca ccgctggtag cggtggtttt   1140
tttgtttgca agcagcagat tacgcgcaga aaaaaaggat ctcaagaaga tcctttgatc   1200
ttttctacgg ggtctgacgc tcagtggaac gaaaactcac gttaagggat tttggtcatg   1260
agattatcaa aaaggatctt cacctagatc cttttaaatt aaaaatgaag ttttaaatca   1320
atctaaagta tatatgagta aacttggtct gacagttacc aatgcttaat cagtgaggca   1380
cctatctcag cgatctgtct atttcgttca tccatagttg cctgactccc cgtcgtgtag   1440
ataactacga tacgggaggg cttaccatct ggccccagtg ctgcaatgat accgcgagac   1500
ccacgctcac cggctccaga tttatcagca ataaaccagc cagccggaag ggccgagcgc   1560
agaagtggtc ctgcaacttt atccgcctcc atccagtcta ttaattgttg ccgggaagct   1620
agagtaagta gttcgccagt taatagtttg cgcaacgttg ttgccattgc tacaggcatc   1680
gtggtgtcac gctcgtcgtt tggtatggct tcattcagct ccggttccca acgatcaagg   1740
cgagttacat gatcccccat gttgtgcaaa aaagcggtta gctccttcgg tcctccgatc   1800
gttgtcagaa gtaagttggc cgcagtgtta tcactcatgg ttatggcagc actgcataat   1860
tctcttactg tcatgccatc cgtaagatgc ttttctgtga ctggtgagta ctcaaccaag   1920
tcattctgag aatagtgtat gcggcgaccg agttgctctt gcccggcgtc aatacgggat   1980
aataccgcgc cacatagcag aactttaaaa gtgctcatca ttggaaaacg ttcttcgggg   2040
cgaaaactct caaggatctt accgctgttg agatccagtt cgatgtaacc cactcgtgca   2100
cccaactgat cttcagcatc ttttactttc accagcgttt ctgggtgagc aaaaacagga   2160
aggcaaaatg ccgcaaaaaa gggaataagg gcgacacgga aatgttgaat actcatactc   2220
ttcctttttc aatattattg aagcatttat cagggttatt gtctcatgag cggatacata   2280
tttgaatgta tttagaaaaa taaacaaata ggggttccgc gcacatttcc ccgaaaagtg   2340
ccacctgacg tccacacaaa aaaccaacac acagatgtaa tgaaaataaa gatattttat   2400
tgcggccatc gtgatggcag gttgggcgtc gcttggtcgg tcatttcgaa ccccagagtc   2460
ccgctcagaa gaactcgtca agaaggcgat agaaggcgat gcgctgcgaa tcgggagcgg   2520
cgataccgta aagcacgagg aagcggtcag cccattcgcc gccaagctct tcagcaatat   2580
cacgggtagc caacgctatg tcctgatagc ggtccgccac acccagccgg ccacagtcga   2640
tgaatccaga aaagcggcca ttttccacca tgatattcgg caagcaggca tcgccatggg   2700
tcacgacgag atcctcgccg tcgggcatgc gcgccttgag cctggcgaac agttcggctg   2760
gcgcgagccc ctgatgctct tcgtccagat catcctgatc gacaagaccg gcttccatcc   2820
gagtacgtgc tcgctcgatg cgatgtttcg cttggtggtc gaatgggcag gtagccggat   2880
caagcgtatg cagccgccgc attgcatcag ccatgatgga tactttctcg gcaggagcaa   2940
ggtgagatga caggagatcc tgccccggca cttcgcccaa tagcagccag tcccttcccg   3000
cttcagtgac aacgtcgagc acagctgcgc aaggaacgcc cgtcgtggcc agccacgata   3060
gccgcgctgc ctcgtcctgc agttcattca gggcaccgga caggtcggtc ttgacaaaaa   3120
gaaccgggcg cccctgcgct gacagccgga acacggcggc atcagagcag ccgattgtct   3180
gttgtgccca gtcatagccg aatagcctct ccacccaagc ggccggagaa cctgcgtgca   3240
atccatcttg ttcaatcata gctcagaggc cgaggcggcc tcggcctctg cataaataaa   3300
aaaaattagt cagccatggg gcggagaatg ggcggaactg ggcggagctc agaggccgag   3360
```

```
gcggcctcgg cctctgcata aataaaaaaa attagtcagc catggggcgg agaatgggcg   3420

gaactgggcg gggatcctca atattggcca ttagccatat tattcattgg ttatatagca   3480

taaatcaata ttggctattg gccattgcat acgttgtatc tatatcataa tatgtacatt   3540

tatattggct catgtccaat atgaccgcca tgttggcatt gattattgac tagttattaa   3600

tagtaatcaa ttacggggtc attagttcat agcccatata tggagttccg cgttacataa   3660

cttacggtaa atggcccgcc tggctgaccg cccaacgacc cccgcccatt gacgtcaata   3720

atgacgtatg ttcccatagt aacgccaata gggactttcc attgacgtca atgggtggag   3780

tatttacggt aaactgccca cttggcagta catcaagtgt atcatatgcc aagtccgccc   3840

cctattgacg tcaatgacgg taaatggccc gcctggcatt atgcccagta catgacctta   3900

cgggactttc ctacttggca gtacatctac gtattagtca tcgctattac catggtgatg   3960

cggttttggc agtacaccaa tgggcgtgga tagcggtttg actcacgggg atttccaagt   4020

ctccacccca ttgacgtcaa tgggagtttg ttttggcacc aaaatcaacg ggactttcca   4080

aaatgtcgta ataaccccgc cccgttgacg caaatgggcg gtaggcgtgt acggtgggag   4140

gtctatataa gcagagctcg tttagtgaac cgtcagatca aaa                     4183
```

<210> SEQ ID NO 2
<211> LENGTH: 5122
<212> TYPE: DNA
<213> ORGANISM: Artificial Sequence
<220> FEATURE:
<223> OTHER INFORMATION: Synthetic oligonucleotide

<400> SEQUENCE: 2

```
gatcccgggc gcagcaccat ggcctgaaat aacctctgaa agaggaactt ggttaggtac     60

cttctgaggc ggaaagaacc agctgtggaa tgtgtgtcag ttagggtgtg gaaagtcccc    120

aggctcccca gcaggcagaa gtatgcaaag catgcatctc aattagtcag caaccaggtg    180

tggaaagtcc ccaggctccc cagcaggcag aagtatgcaa agcatgcatc tcaattagtc    240

agcaaccata gtcccgcccc taactccgcc catcccgccc ctaactccgc ccagttccgc    300

ccattctccg ccccatggct gactaatttt ttttatttat gcagaggccg aggccgcctc    360

ggcctctgag ctattccaga agtagtgagg aggctttttt ggaggcctag gcttttgcaa    420

aaagctgatc ctgagaactt cagggtgagt ttggggaccc ttgattgttc tttctttttc    480

gctattgtaa aattcatgtt atatggaggg ggcaaagttt tcagggtgtt gtttagaatg    540

ggaagatgtc ccttgtatca ccatggaccc tcatgataat ttgtttcttt tcactttcta    600

ctctgttgac aaccattgtc tcctcttatt ttcttttcat tttctgtaac tttttcgtta    660

aactttagct tgcatttgta acgaattttt aaattcactt ttgtttattt gtcagattgt    720

aagtactttc tctaatcact ttttttttcaa ggcaatcagg gtatattata ttgtacttca    780

gcacagtttt agagaacaat tgttataatt aaatgataag gtagaatatt tctgcatata    840

aattctggct ggcgtggaaa tattcttatt ggtagaaaca actacatcct ggtcatcatc    900

ctgcctttct ctttatggtt acaatgatat acactgtttg agatgaggat aaaatactct    960

gagtccaaac cgggcccctc tgctaaccat gttcatgcct tcttcttttt cctacagctc   1020

ctgggcaacg tgctggttgt tgtgctgtct catcattttg gcaaagcgcg ttaacgttac   1080

tggccgaagc cgcttggaat aaggccggtg tgcgtttgtc tatatgtgat tttccaccat   1140

attgccgtct tttggcaatg tgagggcccg gaaacctggc cctgtcttct tgacgagcat   1200

tcctaggggt ctttcccctc tcgccaaagg aatgcaaggt ctgttgaatg tcgtgaagga   1260
```

-continued

```
agcagttcct ctggaagctt cttgaagaca aacaacgtct gtagcgaccc tttgcaggca   1320
gcggaacccc ccacctggcg acaggtgcct ctgcggccaa aagccacgtg tataagatac   1380
acctgcaaag gcggcacaac cccagtgcca cgttgtgagt tggatagttg tggaaagagt   1440
caaatggctc tcctcaagcg tattcaacaa ggggctgaag gatgcccaga aggtacccca   1500
ttgtatggga tctgatctgg ggcctcggtg cacatgcttt acatgtgttt agtcgaggtt   1560
aaaaaaacgt ctaggccccc cgaaccacgg ggacgtggtt ttcctttgaa aaacacgatg   1620
ataatcgatg gcaatcctag cgtgaaggct ggtaggattt tatccccgct gccatcatgg   1680
ttcgaccatt gaactgcatc gtcgccgtgt cccaaaatat ggggattggc aagaacggag   1740
acctaccctg gcctccgctc aggaacgagt tcaagtactt ccaaagaatg accacaacct   1800
cttcagtgga aggtaaacag aatctggtga ttatgggtag gaaaacctgg ttctccattc   1860
ctgagaagaa tcgaccttta aaggacagaa ttaatatagt tctcagtaga gaactcaaag   1920
aaccaccacg aggagctcat ttcttgcca aaagtttgga tgatgcctta agacttattg   1980
aacaaccgga attggcaagt aaagtagaca tggtttggat agtcggaggc agttctgttt   2040
accaggaagc catgaatcaa ccaggccacc tcagactctt tgtgacaagg atcatgcagg   2100
aatttgaaag tgacacgttt ttcccagaaa ttgatttggg gaaatataaa cttctcccag   2160
aatacccagg cgtcctctct gaggtccagg aggaaaaagg catcaagtat aagtttgaag   2220
tctacgagaa gaaagactaa caggaagatg ctttcaagtt ctctgctccc ctcctaaagc   2280
tatgcatttt tataagacca tgggactttt gctggcttta gatcctcgag aatgaatgca   2340
attgttgttg ttaacttgtt tattgcagct tataatggtt acaaataaag caatagcatc   2400
acaaatttca caaataaagc atttttttca ctgcattcta gttgtggttt gtccaaactc   2460
atcaatgtat cttatcatgt ctggataagc ttggcactgg ccgtcgtttt acaacgtcgt   2520
gactgggaaa accctggcgt tacccaactt aatcgccttg cagcacatcc ccctttcgcc   2580
agctggcgta atagcgaaga ggcccgcacc gatcgccctt cccaacagtt gcgcagcctg   2640
aatggcgaat ggcgcctgat gcggtatttt ctccttacgc atctgtgcgg tatttcacac   2700
cgcatatggt gcactctcag tacaatctgc tctgatgccg catagttaag ccagccccga   2760
cacccgccaa cacccgctga cgcgccctga cgggcttgtc tgctcccggc atccgcttac   2820
agacaagctg tgaccgtctc cgggagctgc atgtgtcaga ggttttcacc gtcatcaccg   2880
aaacgcgcga gacgaaaggg cctcgtgata cgcctatttt tataggttaa tgtcatgata   2940
ataatggttt cttagacgtc aggtggcact tttcggggaa atgtgcgcgg aacccctatt   3000
tgtttatttt tctaaataca ttcaaatatg tatccgctca tgagacaata accctgataa   3060
atgcttcaat aatattgaaa aaggaagagt atgagtattc aacatttccg tgtcgccctt   3120
attccctttt ttgcggcatt ttgccttcct gtttttgctc acccagaaac gctggtgaaa   3180
gtaaaagatg ctgaagatca gttgggtgca cgagtgggtt acatcgaact ggatctcaac   3240
agcggtaaga tccttgagag ttttcgcccc gaagaacgtt ttccaatgat gagcactttt   3300
aaagttctgc tatgtggcgc ggtattatcc cgtattgacg ccgggcaaga gcaactcggt   3360
cgccgcatac actattctca gaatgacttg gttgagtact caccagtcac agaaaagcat   3420
cttacggatg gcatgacagt aagagaatta tgcagtgctg ccataaccat gagtgataac   3480
actgcggcca acttacttct gacaacgatc ggaggaccga aggagctaac cgcttttttg   3540
cacaacatgg gggatcatgt aactcgcctt gatcgttggg aaccggagct gaatgaagcc   3600
```

```
ataccaaacg acgagcgtga caccacgatg cctgtagcaa tggcaacaac gttgcgcaaa   3660

ctattaactg gcgaactact tactctagct tcccggcaac aattaataga ctggatggag   3720

gcggataaag ttgcaggacc acttctgcgc tcggcccttc cggctggctg gtttattgct   3780

gataaatctg gagccggtga gcgtgggtct cgcggtatca ttgcagcact ggggccagat   3840

ggtaagccct cccgtatcgt agttatctac acgacgggga gtcaggcaac tatggatgaa   3900

cgaaatagac agatcgctga gataggtgcc tcactgatta agcattggta actgtcagac   3960

caagtttact catatatact ttagattgat ttaaaacttc atttttaatt taaaaggatc   4020

taggtgaaga tcctttttga taatctcatg accaaaatcc cttaacgtga gttttcgttc   4080

cactgagcgt cagaccccgt agaaaagatc aaaggatctt cttgagatcc tttttttctg   4140

cgcgtaatct gctgcttgca aacaaaaaaa ccaccgctac cagcggtggt ttgtttgccg   4200

gatcaagagc taccaactct ttttccgaag gtaactggct tcagcagagc gcagatacca   4260

aatactgtcc ttctagtgta gccgtagtta ggccaccact tcaagaactc tgtagcaccg   4320

cctacatacc tcgctctgct aatcctgtta ccagtggctg ctgccagtgg cgataagtcg   4380

tgtcttaccg ggttggactc aagacgatag ttaccggata aggcgcagcg gtcgggctga   4440

acggggggtt cgtgcacaca gcccagcttg gagcgaacga cctacaccga actgagatac   4500

ctacagcgtg agctatgaga aagcgccacg cttcccgaag ggagaaaggc ggacaggtat   4560

ccggtaagcg gcagggtcgg aacaggagag cgcacgaggg agcttccagg gggaaacgcc   4620

tggtatcttt atagtcctgt cgggtttcgc cacctctgac ttgagcgtcg atttttgtga   4680

tgctcgtcag gggggcggag cctatggaaa aacgccagca acgcggcctt tttacggttc   4740

ctggcctttt gctggccttt tgctcacatg ttctttcctg cgttatcccc tgattctgtg   4800

gataaccgta ttaccgcctt tgagtgagct gataccgctc gccgcagccg aacgaccgag   4860

cgcagcgagt cagtgagcga ggaagcggaa gagcgcccaa tacgcaaacc gcctctcccc   4920

gcgcgttggc cgattcatta atgcagctgg cacgacaggt ttcccgactg gaaagcgggc   4980

agtgagcgca acgcaattaa tgtgagttag ctcactcatt aggcacccca ggctttacac   5040

tttatgcttc cggctcgtat gttgtgtgga attgtgagcg gataacaatt tcacacagga   5100

aacagctatg accatgatta cg                                            5122
```

<210> SEQ ID NO 3
<211> LENGTH: 4827
<212> TYPE: DNA
<213> ORGANISM: Artificial Sequence
<220> FEATURE:
<223> OTHER INFORMATION: Synthetic oligonucleotide

<400> SEQUENCE: 3

```
ccggtgccac catggcccct ggctcccgga cctccctgct gctggccttc ggcctgctgt     60

gcctgccttg gctgcaggaa ggctccgcct tccctaccat ccctctgtcc cggctgttcg    120

acaacgccat gctgcgggcc caccggctgc accagctggc ctttgacacc taccaggaat    180

ttgaggaagc ctacatccct aaggaacaga agtactcctt cctgcagaac cctcagacca    240

gcctgtgctt ctccgagtcc atccctaccc cttccaaccg ggaggaaaca cagcagaagt    300

ccaacctgga gctgctgcgg atcagcctgc tgctgatcca gtcctggctg gagcctgtgc    360

agttcctgcg gtccgtgttc gccaactccc tggtgtacgg cgcctccgac tccaacgtgt    420

acgacctgct gaaggacctg gaggaaggca tccagaccct gatgggcaga ctggaggacg    480

gctcccctcg gaccggccag atcttcaagc agacctactc caagttcgac accaactccc    540
```

```
acaacgacga cgccctgctg aagaactatg gcctgctgta ctgcttccgg aaggacatgg    600
acaaggtgga gacattcctg cggatcgtgc agtgccggtc cgtggagggc tcctgcggct    660
tctgagatat caatgaatgc aattgttgtt gttaacttgt ttattgcagc ttataatggt    720
tacaaataaa gcaatagcat cacaaatttc acaaataaag catttttttc actgcattct    780
agttgtggtt tgtccaaact catcaatgta tcttatcatg tctgaattcg taatcatggt    840
catagctgtt tcctgtgtga aattgttatc cgctcacaat tccacacaac atacgagccg    900
gaagcataaa gtgtaaagcc tggggtgcct aatgagtgag ctaactcaca ttaattgcgt    960
tgcgctcact gcccgctttc cagtcgggaa acctgtcgtg ccagctgcat taatgaatcg   1020
gccaacgcgc ggggagaggc ggtttgcgta ttgggcgctc ttccgcttcc tcgctcactg   1080
actcgctgcg ctcggtcgtt cggctgcggc gagcggtatc agctcactca aaggcggtaa   1140
tacggttatc cacagaatca ggggataacg caggaaagaa catgtgagca aaaggccagc   1200
aaaaggccag gaaccgtaaa aaggccgcgt tgctggcgtt tttccatagg ctccgccccc   1260
ctgacgagca tcacaaaaat cgacgctcaa gtcagaggtg gcgaaacccg acaggactat   1320
aaagatacca ggcgtttccc cctggaagct ccctcgtgcg ctctcctgtt ccgaccctgc   1380
cgcttaccgg atacctgtcc gcctttctcc cttcgggaag cgtggcgctt tctcatagct   1440
cacgctgtag gtatctcagt tcggtgtagg tcgttcgctc caagctgggc tgtgtgcacg   1500
aacccccgt tcagcccgac cgctgcgcct tatccggtaa ctatcgtctt gagtccaacc   1560
cggtaagaca cgacttatcg ccactggcag cagccactgg taacaggatt agcagagcga   1620
ggtatgtagg cggtgctaca gagttcttga agtggtggcc taactacggc tacactagaa   1680
ggacagtatt tggtatctgc gctctgctga agccagttac cttcggaaaa agagttggta   1740
gctcttgatc cggcaaacaa accaccgctg gtagcggtgg tttttttgtt tgcaagcagc   1800
agattacgcg cagaaaaaaa ggatctcaag aagatccttt gatcttttct acggggtctg   1860
acgctcagtg gaacgaaaac tcacgttaag ggattttggt catgagatta tcaaaaagga   1920
tcttcaccta gatcctttta aattaaaaat gaagttttaa atcaatctaa agtatatatg   1980
agtaaacttg gtctgacagt taccaatgct taatcagtga ggcacctatc tcagcgatct   2040
gtctatttcg ttcatccata gttgcctgac tccccgtcgt gtagataact acgatacggg   2100
agggcttacc atctggcccc agtgctgcaa tgataccgcg agacccacgc tcaccggctc   2160
cagatttatc agcaataaac cagccagccg gaagggccga gcgcagaagt ggtcctgcaa   2220
ctttatccgc ctccatccag tctattaatt gttgccggga agctagagta agtagttcgc   2280
cagttaatag tttgcgcaac gttgttgcca ttgctacagg catcgtggtg tcacgctcgt   2340
cgtttggtat ggcttcattc agctccggtt cccaacgatc aaggcgagtt acatgatccc   2400
ccatgttgtg caaaaaagcg gttagctcct tcggtcctcc gatcgttgtc agaagtaagt   2460
tggccgcagt gttatcactc atggttatgg cagcactgca taattctctt actgtcatgc   2520
catccgtaag atgcttttct gtgactggtg agtactcaac caagtcattc tgagaatagt   2580
gtatgcggcg accgagttgc tcttgcccgg cgtcaatacg ggataatacc gcgccacata   2640
gcagaacttt aaaagtgctc atcattggaa aacgttcttc ggggcgaaaa ctctcaagga   2700
tcttaccgct gttgagatcc agttcgatgt aacccactcg tgcacccaac tgatcttcag   2760
catcttttac tttcaccagc gtttctgggt gagcaaaaac aggaaggcaa aatgccgcaa   2820
aaaagggaat aagggcgaca cggaaatgtt gaatactcat actcttcctt tttcaatatt   2880
```

```
attgaagcat ttatcagggt tattgtctca tgagcggata catatttgaa tgtatttaga   2940

aaaataaaca aataggggtt ccgcgcacat ttccccgaaa agtgccacct gacgtccaca   3000

caaaaaacca acacacagat gtaatgaaaa taaagatatt ttattgcggc catcgtgatg   3060

gcaggttggg cgtcgcttgg tcggtcattt cgaaccccag agtcccgctc agaagaactc   3120

gtcaagaagg cgatagaagg cgatgcgctg cgaatcggga gcggcgatac cgtaaagcac   3180

gaggaagcgg tcagcccatt cgccgccaag ctcttcagca atatcacggg tagccaacgc   3240

tatgtcctga tagcggtccg ccacacccag ccggccacag tcgatgaatc cagaaaagcg   3300

gccattttcc accatgatat tcggcaagca ggcatcgcca tgggtcacga cgagatcctc   3360

gccgtcgggc atgcgcgcct tgagcctggc gaacagttcg gctggcgcga gcccctgatg   3420

ctcttcgtcc agatcatcct gatcgacaag accggcttcc atccgagtac gtgctcgctc   3480

gatgcgatgt ttcgcttggt ggtcgaatgg gcaggtagcc ggatcaagcg tatgcagccg   3540

ccgcattgca tcagccatga tggatacttt ctcggcagga gcaaggtgag atgacaggag   3600

atcctgcccc ggcacttcgc ccaatagcag ccagtccctt cccgcttcag tgacaacgtc   3660

gagcacagct gcgcaaggaa cgcccgtcgt ggccagccac gatagccgcg ctgcctcgtc   3720

ctgcagttca ttcagggcac cggacaggtc ggtcttgaca aaaagaaccg ggcgcccctg   3780

cgctgacagc cggaacacgg cggcatcaga gcagccgatt gtctgttgtg cccagtcata   3840

gccgaatagc ctctccaccc aagcggccgg agaacctgcg tgcaatccat cttgttcaat   3900

catagctcag aggccgaggc ggcctcggcc tctgcataaa taaaaaaaat tagtcagcca   3960

tggggcggag aatgggcgga actgggcgga gctcagaggc cgaggcggcc tcggcctctg   4020

cataaataaa aaaaattagt cagccatggg gcggagaatg ggcggaactg ggcggggatc   4080

ctcaatattg gccattagcc atattattca ttggttatat agcataaatc aatattggct   4140

attggccatt gcatacgttg tatctatatc ataatatgta catttatatt ggctcatgtc   4200

caatatgacc gccatgttgg cattgattat tgactagtta ttaatagtaa tcaattacgg   4260

ggtcattagt tcatagccca tatatggagt tccgcgttac ataacttacg gtaaatggcc   4320

cgcctggctg accgcccaac gacccccgcc cattgacgtc aataatgacg tatgttccca   4380

tagtaacgcc aatagggact ttccattgac gtcaatgggt ggagtattta cggtaaactg   4440

cccacttggc agtacatcaa gtgtatcata tgccaagtcc gccccctatt gacgtcaatg   4500

acggtaaatg gcccgcctgg cattatgccc agtacatgac cttacgggac tttcctactt   4560

ggcagtacat ctacgtatta gtcatcgcta ttaccatggt gatgcggttt tggcagtaca   4620

ccaatgggcg tggatagcgg tttgactcac ggggatttcc aagtctccac cccattgacg   4680

tcaatgggag tttgttttgg caccaaaatc aacgggactt tccaaaatgt cgtaataacc   4740

ccgccccgtt gacgcaaatg ggcggtaggc gtgtacggtg ggaggtctat ataagcagag   4800

ctcgtttagt gaaccgtcag atcaaaa                                        4827
```

<210> SEQ ID NO 4
<211> LENGTH: 5026
<212> TYPE: DNA
<213> ORGANISM: Artificial Sequence
<220> FEATURE:
<223> OTHER INFORMATION: Synthetic oligonucleotide

<400> SEQUENCE: 4

```
gacgaaaggg cctcgtgata cgcctatttt tataggttaa tgtcatgata ataatggttt     60

cttagacgtc aggtggcact tttcggggaa atgtgcgcgg aacccctatt tgtttatttt    120
```

```
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgaattccag ctgtggaatg tgtgtcagtt agggtgtgga aagtccccag   2280
gctccccagc aggcagaagt atgcaaagca tgcatctcaa ttagtcagca accaggtgtg   2340
gaaagtcccc aggctcccca gcaggcagaa gtatgcaaag catgcatctc aattagtcag   2400
caaccatagt cccgccccta actccgccca tcccgcccct aactccgccc agttccgccc   2460
```

```
attctccgcc ccatggctga ctaatttttt ttatttatgc agaggccgag gccgcctcgg   2520
cctctgagct attccagaag tagtgaggag gcttttttgg aggcctaggc ttttgcaaaa   2580
agcgatcctg agaacttcag ggtgagtttg gggacccttg attgttcttt ctttttcgct   2640
attgtaaaat tcatgttata tggagggggc aaagttttca gggtgttgtt tagaatggga   2700
agatgtccct tgtatcacca tggaccctca tgataatttt gtttctttca ctttctactc   2760
tgttgacaac cattgtctcc tcttattttc ttttcatttt ctgtaacttt ttcgttaaac   2820
tttagcttgc atttgtaacg aatttttaaa ttcacttttg tttatttgtc agattgtaag   2880
tactttctct aatcactttt ttttcaaggc aatcagggta tattatattg tacttcagca   2940
cagttttaga gaacaattgt tataattaaa tgataaggta gaatatttct gcatataaat   3000
tctggctggc gtggaaatat tcttattggt agaaacaact acatcctggt catcatcctg   3060
cctttctctt tatggttaca atgatataca ctgtttgaga tgaggataaa atactctgag   3120
tccaaaccgg gcccctctgc taaccatgtt catgccttct tctttttcct acagctcctg   3180
ggcaacgtgc tggttgttgt gctgtctcat cattttggca aaaccggtta gtgatatcaa   3240
tgaatgcaat tgttgttgtt aacttgttta ttgcagctta taatggttac aaataaagca   3300
atagcatcac aaatttcaca aataaagcat ttttttcact gcattctagt tgtggtttgt   3360
ccaaactcat caatgtatct tatcatgtct ggatcccggg gatcctctag acagctgtgg   3420
aatgtgtgtc agttagggtg tggaaagtcc ccaggctccc cagcaggcag aagtatgcaa   3480
agcatgcatc tcaattagtc agcaaccagg tgtggaaagt ccccaggctc cccagcaggc   3540
agaagtatgc aaagcatgca tctcaattag tcagcaacca tagtcccgcc cctaactccg   3600
cccatcccgc ccctaactcc gcccagttcc gcccattctc cgccccatgg ctgactaatt   3660
ttttttattt atgcagaggc cgaggccgcc tcggcctctg agctattcca gaagtagtga   3720
ggaggctttt ttggaggcct aggcttttgc aaaaagctca tcgatggcaa tcctagcgtg   3780
aaggctggta ggattttatc cccgctgcca tcatggttcg accattgaac tgcatcgtcg   3840
ccgtgtccca aaatatgggg attggcaaga acggagacct accctggcct ccgctcagga   3900
acgagttcaa gtacttccaa agaatgacca caacctcttc agtggaaggt aaacagaatc   3960
tggtgattat gggtaggaaa acctggttct ccattcctga gaagaatcga cctttaaagg   4020
acagaattaa tatagttctc agtagagaac tcaaagaacc accacgagga gctcattttc   4080
ttgccaaaag tttggatgat gccttaagac ttattgaaca accggaattg gcaagtaaag   4140
tagacatggt ttggatagtc ggaggcagtt ctgtttacca ggaagccatg aatcaaccag   4200
gccacctcag actctttgtg acaaggatca tgcaggaatt tgaaagtgac acgtttttcc   4260
cagaaattga tttggggaaa tataaacttc tcccagaata cccaggcgtc ctctctgagg   4320
tccaggagga aaaaggcatc aagtataagt ttgaagtcta cgagaagaaa gactaacagg   4380
aagatgcttt caagttctct gctcccctcc taaagctatg catttttata agaccatggg   4440
acttttgctg gctttagatc ctcgagaatg aatgcaattg ttgttgttaa cttgtttatt   4500
gcagcttata atggttacaa ataaagcaat agcatcacaa atttcacaaa taaagcattt   4560
ttttcactgc attctagttg tggtttgtcc aaactcatca atgtatctta tcatgtctgg   4620
ataagcttgg cactggccgt cgttttacaa cgtcgtgact gggaaaaccc tggcgttacc   4680
caacttaatc gccttgcagc acatccccct ttcgccagct ggcgtaatag cgaagaggcc   4740
cgcaccgatc gcccttccca acagttgcgc agcctgaatg gcgaatggcg cctgatgcgg   4800
tattttctcc ttacgcatct gtgcggtatt tcacaccgca tatggtgcac tctcagtaca   4860
```

```
atctgctctg atgccgcata gttaagccag ccccgacacc cgccaacacc cgctgacgcg   4920

ccctgacggg cttgtctgct cccggcatcc gcttacagac aagctgtgac cgtctccggg   4980

agctgcatgt gtcagaggtt ttcaccgtca tcaccgaaac gcgcga                  5026


<210> SEQ ID NO 5
<211> LENGTH: 5133
<212> TYPE: DNA
<213> ORGANISM: Artificial Sequence
<220> FEATURE:
<223> OTHER INFORMATION: Synthetic oligonucleotide

<400> SEQUENCE: 5

cgatggcaat cctagcgtga aggctggtag gattttatcc ccgctgccat catggttcga     60

ccattgaact gcatcgtcgc cgtgtcccaa aatatgggga ttggcaagaa cggagaccta    120

ccctggcctc cgctcaggaa cgagttcaag tacttccaaa gaatgaccac aacctcttca    180

gtggaaggta aacagaatct ggtgattatg ggtaggaaaa cctggttctc cattcctgag    240

aagaatcgac ctttaaagga cagaattaat atagttctca gtagagaact caaagaacca    300

ccacgaggag ctcattttct tgccaaaagt ttggatgatg ccttaagact tattgaacaa    360

ccggaattgg caagtaaagt agacatggtt tggatagtcg gaggcagttc tgtttaccag    420

gaagccatga atcaaccagg ccacctcaga ctctttgtga caaggatcat gcaggaattt    480

gaaagtgaca cgtttttccc agaaattgat ttggggaaat ataaacttct cccagaatac    540

ccaggcgtcc tctctgaggt ccaggaggaa aaaggcatca agtataagtt tgaagtctac    600

gagaagaaag actaacagga agatgctttc aagttctctg ctcccctcct aaagctatgc    660

atttttataa gaccatggga cttttgctgg ctttagatcc tcgagaatga atgcaattgt    720

tgttgttaac ttgtttattg cagcttataa tggttacaaa taaagcaata gcatcacaaa    780

tttcacaaat aaagcatttt tttcactgca ttctagttgt ggtttgtcca aactcatcaa    840

tgtatcttat catgtctgga taagcttggc actggccgtc gttttacaac gtcgtgactg    900

ggaaaaccct ggcgttaccc aacttaatcg ccttgcagca catccccctt tcgccagctg    960

gcgtaatagc gaagaggccc gcaccgatcg cccttcccaa cagttgcgca gcctgaatgg   1020

cgaatggcgc ctgatgcggt attttctcct tacgcatctg tgcggtattt cacaccgcat   1080

atggtgcact ctcagtacaa tctgctctga tgccgcatag ttaagccagc cccgacaccc   1140

gccaacaccc gctgacgcgc cctgacgggc ttgtctgctc ccggcatccg cttacagaca   1200

agctgtgacc gtctccggga gctgcatgtg tcagaggttt tcaccgtcat caccgaaacg   1260

cgcgagacga aagggcctcg tgatacgcct atttttatag gttaatgtca tgataataat   1320

ggtttcttag acgtcaggtg gcacttttcg gggaaatgtg cgcggaaccc ctatttgttt   1380

atttttctaa atacattcaa atatgtatcc gctcatgaga caataaccct gataaatgct   1440

tcaataatat tgaaaaagga agagtatgag tattcaacat ttccgtgtcg cccttattcc   1500

cttttttgcg gcattttgcc ttcctgtttt tgctcaccca gaaacgctgg tgaaagtaaa   1560

agatgctgaa gatcagttgg gtgcacgagt gggttacatc gaactggatc tcaacagcgg   1620

taagatcctt gagagttttc gccccgaaga acgttttcca atgatgagca cttttaaagt   1680

tctgctatgt ggcgcggtat tatcccgtat tgacgccggg caagagcaac tcggtcgccg   1740

catacactat tctcagaatg acttggttga gtactcacca gtcacagaaa agcatcttac   1800

ggatggcatg acagtaagag aattatgcag tgctgccata accatgagtg ataacactgc   1860
```

```
ggccaactta cttctgacaa cgatcggagg accgaaggag ctaaccgctt ttttgcacaa   1920
catgggggat catgtaactc gccttgatcg ttgggaaccg gagctgaatg aagccatacc   1980
aaacgacgag cgtgacacca cgatgcctgt agcaatggca acaacgttgc gcaaactatt   2040
aactggcgaa ctacttactc tagcttcccg gcaacaatta atagactgga tggaggcgga   2100
taaagttgca ggaccacttc tgcgctcggc ccttccggct ggctggttta ttgctgataa   2160
atctggagcc ggtgagcgtg ggtctcgcgg tatcattgca gcactggggc cagatggtaa   2220
gccctcccgt atcgtagtta tctacacgac ggggagtcag gcaactatgg atgaacgaaa   2280
tagacagatc gctgagatag gtgcctcact gattaagcat tggtaactgt cagaccaagt   2340
ttactcatat atactttaga ttgatttaaa acttcatttt taatttaaaa ggatctaggt   2400
gaagatcctt tttgataatc tcatgaccaa aatcccttaa cgtgagtttt cgttccactg   2460
agcgtcagac cccgtagaaa agatcaaagg atcttcttga gatccttttt ttctgcgcgt   2520
aatctgctgc ttgcaaacaa aaaaaccacc gctaccagcg gtggtttgtt tgccggatca   2580
agagctacca actctttttc cgaaggtaac tggcttcagc agagcgcaga taccaaatac   2640
tgtccttcta gtgtagccgt agttaggcca ccacttcaag aactctgtag caccgcctac   2700
atacctcgct ctgctaatcc tgttaccagt ggctgctgcc agtggcgata agtcgtgtct   2760
taccgggttg gactcaagac gatagttacc ggataaggcg cagcggtcgg gctgaacggg   2820
gggttcgtgc acacagccca gcttggagcg aacgacctac accgaactga gatacctaca   2880
gcgtgagcta tgagaaagcg ccacgcttcc cgaagggaga aaggcggaca ggtatccggt   2940
aagcggcagg gtcggaacag gagagcgcac gagggagctt ccagggggaa acgcctggta   3000
tctttatagt cctgtcgggt ttcgccacct ctgacttgag cgtcgatttt tgtgatgctc   3060
gtcagggggg cggagcctat ggaaaaacgc cagcaacgcg gcctttttac ggttcctggc   3120
cttttgctgg ccttttgctc acatgttctt tcctgcgtta tcccctgatt ctgtggataa   3180
ccgtattacc gcctttgagt gagctgatac cgctcgccgc agccgaacga ccgagcgcag   3240
cgagtcagtg agcgaggaag cggaagagcg cccaatacgc aaaccgcctc tccccgcgcg   3300
ttggccgatt cattaatgca gctggcacga caggtttccc gactggaaag cgggcagtga   3360
gcgcaacgca attaatgtga gttagctcac tcattaggca ccccaggctt tacactttat   3420
gcttccggct cgtatgttgt gtggaattgt gagcggataa caatttcaca caggaaacag   3480
ctatgaccat gattacggat cccgggcgca gcaccatggc ctgaaataac ctctgaaaga   3540
ggaacttggt taggtacctt ctgaggcgga aagaaccagc tgtggaatgt gtgtcagtta   3600
gggtgtggaa agtccccagg ctccccagca ggcagaagta tgcaaagcat gcatctcaat   3660
tagtcagcaa ccaggtgtgg aaagtcccca ggctccccag caggcagaag tatgcaaagc   3720
atgcatctca attagtcagc aaccatagtc ccgcccctaa ctccgcccat cccgccccta   3780
actccgccca gttccgccca ttctccgccc catggctgac taattttttt tatttatgca   3840
gaggccgagg ccgcctcggc ctctgagcta ttccagaagt agtgaggagg cttttttgga   3900
ggcctaggct tttgcaaaaa gctgatcctg agaacttcag ggtgagtttg gggacccttg   3960
attgttcttt ctttttcgct attgtaaaat tcatgttata tggagggggc aaagttttca   4020
gggtgttgtt tagaatggga agatgtccct tgtatcacca tggaccctca tgataatttt   4080
gtttctttca ctttctactc tgttgacaac cattgtctcc tcttattttc ttttcatttt   4140
ctgtaacttt ttcgttaaac tttagcttgc atttgtaacg aatttttaaa ttcacttttg   4200
tttatttgtc agattgtaag tactttctct aatcactttt ttttcaaggc aatcagggta   4260
```

```
tattatattg tacttcagca cagttttaga gaacaattgt tataattaaa tgataaggta   4320

gaatatttct gcatataaat tctggctggc gtggaaatat tcttattggt agaaacaact   4380

acatcctggt catcatcctg cctttctctt tatggttaca atgatataca ctgtttgaga   4440

tgaggataaa atactctgag tccaaaccgg gcccctctgc taaccatgtt catgccttct   4500

tctttttcct acagctcctg ggcaacgtgc tggttgttgt gctgtctcat cattttggca   4560

aagtcgacga cgaacgcgtt aacgttactg gccgaagccg cttggaataa ggccggtgtg   4620

cgtttgtcta tatgtgattt tccaccatat tgccgtcttt tggcaatgtg agggcccgga   4680

aacctggccc tgtcttcttg acgagcattc ctaggggtct ttcccctctc gccaaaggaa   4740

tgcaaggtct gttgaatgtc gtgaaggaag cagttcctct ggaagcttct tgaagacaaa   4800

caacgtctgt agcgaccctt tgcaggcagc ggaacccccc acctggcgac aggtgcctct   4860

gcggccaaaa gccacgtgta taagatacac ctgcaaaggc ggcacaaccc cagtgccacg   4920

ttgtgagttg gatagttgtg gaaagagtca aatggctctc ctcaagcgta ttcaacaagg   4980

ggctgaagga tgcccagaag gtaccccatt gtatgggatc tgatctgggg cctcggtgca   5040

catgctttac atgtgtttag tcgaggttaa aaaaacgtct aggccccccg aaccacgggg   5100

acgtggtttt cctttgaaaa acacgatgat aat                                5133
```

<210> SEQ ID NO 6
<211> LENGTH: 6250
<212> TYPE: DNA
<213> ORGANISM: Artificial Sequence
<220> FEATURE:
<223> OTHER INFORMATION: Synthetic oligonucleotide

<400> SEQUENCE: 6

```
gacgaaaggg cctcgtgata cgcctatttt tataggttaa tgtcatgata ataatggttt     60

cttagacgtc aggtggcact tttcggggaa atgtgcgcgg aacccctatt tgtttatttt    120

tctaaataca ttcaaatatg tatccgctca tgagacaata accctgataa atgcttcaat    180

aatattgaaa aaggaagagt atgagtattc aacatttccg tgtcgccctt attccctttt    240

ttgcggcatt ttgccttcct gtttttgctc acccagaaac gctggtgaaa gtaaaagatg    300

ctgaagatca gttgggtgca cgagtgggtt acatcgaact ggatctcaac agcggtaaga    360

tccttgagag ttttcgcccc gaagaacgtt ttccaatgat gagcactttt aaagttctgc    420

tatgtggcgc ggtattatcc cgtattgacg ccgggcaaga gcaactcggt cgccgcatac    480

actattctca gaatgacttg gttgagtact caccagtcac agaaaagcat cttacggatg    540

gcatgacagt aagagaatta tgcagtgctg ccataaccat gagtgataac actgcggcca    600

acttacttct gacaacgatc ggaggaccga aggagctaac cgcttttttg cacaacatgg    660

gggatcatgt aactcgcctt gatcgttggg aaccggagct gaatgaagcc ataccaaacg    720

acgagcgtga caccacgatg cctgtagcaa tggcaacaac gttgcgcaaa ctattaactg    780

gcgaactact tactctagct tcccggcaac aattaataga ctggatggag gcggataaag    840

ttgcaggacc acttctgcgc tcggcccttc cggctggctg gtttattgct gataaatctg    900

gagccggtga gcgtgggtct cgcggtatca ttgcagcact ggggccagat ggtaagccct    960

cccgtatcgt agttatctac acgacgggga gtcaggcaac tatggatgaa cgaaatagac   1020

agatcgctga gataggtgcc tcactgatta agcattggta actgtcagac caagtttact   1080

catatatact ttagattgat ttaaaacttc atttttaatt taaaaggatc taggtgaaga   1140
```

```
tccttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgaattccag ctgtggaatg tgtgtcagtt agggtgtgga aagtccccag   2280
gctccccagc aggcagaagt atgcaaagca tgcatctcaa ttagtcagca accaggtgtg   2340
gaaagtcccc aggctcccca gcaggcagaa gtatgcaaag catgcatctc aattagtcag   2400
caaccatagt cccgccccta actccgccca tcccgcccct aactccgccc agttccgccc   2460
attctccgcc ccatggctga ctaatttttt ttatttatgc agaggccgag gccgcctcgg   2520
cctctgagct attccagaag tagtgaggag gcttttttgg aggcctaggc ttttgcaaaa   2580
agcgatcctg agaacttcag ggtgagtttg gggacccttg attgttcttt ctttttcgct   2640
attgtaaaat tcatgttata tggagggggc aaagttttca gggtgttgtt tagaatggga   2700
agatgtccct tgtatcacca tggaccctca tgataatttt gtttctttca ctttctactc   2760
tgttgacaac cattgtctcc tcttattttc ttttcatttt ctgtaacttt ttcgttaaac   2820
tttagcttgc atttgtaacg aatttttaaa ttcacttttg tttatttgtc agattgtaag   2880
tactttctct aatcactttt ttttcaaggc aatcagggta tattatattg tacttcagca   2940
cagttttaga gaacaattgt tataattaaa tgataaggta gaatatttct gcatataaat   3000
tctggctggc gtggaaatat tcttattggt agaaacaact acatcctggt catcatcctg   3060
cctttctctt tatggttaca atgatataca ctgtttgaga tgaggataaa atactctgag   3120
tccaaaccgg gcccctctgc taaccatgtt catgccttct tctttttcct acagctcctg   3180
ggcaacgtgc tggttgttgt gctgtctcat cattttggca aaaccggtta gtgatatcaa   3240
tgaatgcaat tgttgttgtt aacttgttta ttgcagctta taatggttac aaataaagca   3300
atagcatcac aaatttcaca aataaagcat ttttttcact gcattctagt tgtggtttgt   3360
ccaaactcat caatgtatct tatcatgtct ggatcccggg cgcagcacca tggcctgaaa   3420
taacctctga aagaggaact tggttaggta ccttctgagg cggaaagaac cagctgtgga   3480
atgtgtgtca gttagggtgt ggaaagtccc caggctcccc agcaggcaga agtatgcaaa   3540
```

```
gcatgcatct caattagtca gcaaccaggt gtggaaagtc cccaggctcc ccagcaggca   3600
gaagtatgca aagcatgcat ctcaattagt cagcaaccat agtcccgccc ctaactccgc   3660
ccatcccgcc cctaactccg cccagttccg cccattctcc gccccatggc tgactaattt   3720
tttttattta tgcagaggcc gaggccgcct cggcctctga gctattccag aagtagtgag   3780
gaggcttttt tggaggccta ggcttttgca aaaagctgat cctgagaact tcagggtgag   3840
tttggggacc cttgattgtt ctttcttttt cgctattgta aaattcatgt tatatggagg   3900
gggcaaagtt ttcagggtgt tgtttagaat gggaagatgt cccttgtatc accatggacc   3960
ctcatgataa ttttgtttct ttcactttct actctgttga caaccattgt ctcctcttat   4020
tttcttttca ttttctgtaa ctttttcgtt aaactttagc ttgcatttgt aacgaatttt   4080
taaattcact tttgtttatt tgtcagattg taagtacttt ctctaatcac tttttttca    4140
aggcaatcag ggtatattat attgtacttc agcacagttt tagagaacaa ttgttataat   4200
taaatgataa ggtagaatat ttctgcatat aaattctggc tggcgtggaa atattcttat   4260
tggtagaaac aactacatcc tggtcatcat cctgcctttc tctttatggt tacaatgata   4320
tacactgttt gagatgagga taaaatactc tgagtccaaa ccgggcccct ctgctaacca   4380
tgttcatgcc ttcttctttt tcctacagct cctgggcaac gtgctggttg ttgtgctgtc   4440
tcatcatttt ggcaaagtcg acgacgaacg cgtaatgaat gcaattgttg ttgttaactt   4500
gtttattgca gcttataatg gttacaaata aagcaatagc atcacaaatt tcacaaataa   4560
agcatttttt tcactgcatt ctagttgtgg tttgtccaaa ctcatcaatg tatcttatca   4620
tgtctggatt ctagacagct gtggaatgtg tgtcagttag ggtgtggaaa gtccccaggc   4680
tccccagcag gcagaagtat gcaaagcatg catctcaatt agtcagcaac caggtgtgga   4740
aagtccccag gctccccagc aggcagaagt atgcaaagca tgcatctcaa ttagtcagca   4800
accatagtcc cgcccctaac tccgcccatc ccgcccctaa ctccgcccag ttccgcccat   4860
tctccgcccc atggctgact aatttttttt atttatgcag aggccgaggc cgcctcggcc   4920
tctgagctat tccagaagta gtgaggaggc ttttttggag gcctaggctt ttgcaaaaag   4980
ctcatcgatg gcaatcctag cgtgaaggct ggtaggattt tatccccgct gccatcatgg   5040
ttcgaccatt gaactgcatc gtcgccgtgt cccaaaatat ggggattggc aagaacggag   5100
acctaccctg gcctccgctc aggaacgagt tcaagtactt ccaaagaatg accacaacct   5160
cttcagtgga aggtaaacag aatctggtga ttatgggtag gaaaacctgg ttctccattc   5220
ctgagaagaa tcgaccttta aaggacagaa ttaatatagt tctcagtaga gaactcaaag   5280
aaccaccacg aggagctcat ttcttgcca aaagtttgga tgatgcctta agacttattg    5340
aacaaccgga attggcaagt aaagtagaca tggtttggat agtcggaggc agttctgttt   5400
accaggaagc catgaatcaa ccaggccacc tcagactctt tgtgacaagg atcatgcagg   5460
aatttgaaag tgacacgttt ttcccagaaa ttgatttggg gaaatataaa cttctcccag   5520
aatacccagg cgtcctctct gaggtccagg aggaaaaagg catcaagtat aagtttgaag   5580
tctacgagaa gaaagactaa caggaagatg ctttcaagtt ctctgctccc ctcctaaagc   5640
tatgcatttt tataagacca tgggactttt gctggcttta gatcctcgag aatgaatgca   5700
attgttgttg ttaacttgtt tattgcagct tataatggtt acaaataaag caatagcatc   5760
acaaatttca caaataaagc atttttttca ctgcattcta gttgtggttt gtccaaactc   5820
atcaatgtat cttatcatgt ctggataagc ttggcactgg ccgtcgtttt acaacgtcgt   5880
```

gactgggaaa accctggcgt tacccaactt aatcgccttg cagcacatcc ccctttcgcc 5940
agctggcgta atagcgaaga ggcccgcacc gatcgccctt cccaacagtt gcgcagcctg 6000
aatggcgaat ggcgcctgat gcggtatttt ctccttacgc atctgtgcgg tatttcacac 6060
cgcatatggt gcactctcag tacaatctgc tctgatgccg catagttaag ccagccccga 6120
cacccgccaa cacccgctga cgcgccctga cgggcttgtc tgctcccggc atccgcttac 6180
agacaagctg tgaccgtctc cgggagctgc atgtgtcaga ggttttcacc gtcatcaccg 6240
aaacgcgcga 6250

<210> SEQ ID NO 7
<211> LENGTH: 6064
<212> TYPE: DNA
<213> ORGANISM: Artificial Sequence
<220> FEATURE:
<223> OTHER INFORMATION: Synthetic oligonucleotide

<400> SEQUENCE: 7
gatcccgggc gcagcaccat ggcctgaaat aacctctgaa agaggaactt ggttaggtac 60
cttctgaggc ggaaagaacc agctgtggaa tgtgtgtcag ttagggtgtg gaaagtcccc 120
aggctcccca gcaggcagaa gtatgcaaag catgcatctc aattagtcag caaccaggtg 180
tggaaagtcc ccaggctccc cagcaggcag aagtatgcaa agcatgcatc tcaattagtc 240
agcaaccata gtcccgcccc taactccgcc catcccgccc ctaactccgc ccagttccgc 300
ccattctccg ccccatggct gactaatttt ttttatttat gcagaggccg aggccgcctc 360
ggcctctgag ctattccaga agtagtgagg aggctttttt ggaggcctag gcttttgcaa 420
aaagctgatc ctgagaactt cagggtgagt ttggggaccc ttgattgttc tttctttttc 480
gctattgtaa aattcatgtt atatggaggg ggcaaagttt tcagggtgtt gtttagaatg 540
ggaagatgtc ccttgtatca ccatggaccc tcatgataat ttgtttcttt tcactttcta 600
ctctgttgac aaccattgtc tcctcttatt ttcttttcat tttctgtaac tttttcgtta 660
aactttagct tgcatttgta acgaattttt aaattcactt ttgtttattt gtcagattgt 720
aagtactttc tctaatcact tttttttcaa ggcaatcagg gtatattata ttgtacttca 780
gcacagtttt agagaacaat tgttataatt aaatgataag gtagaatatt tctgcatata 840
aattctggct ggcgtggaaa tattcttatt ggtagaaaca actacatcct ggtcatcatc 900
ctgcctttct ctttatggtt acaatgatat acactgtttg agatgaggat aaaatactct 960
gagtccaaac cgggcccctc tgctaaccat gttcatgcct tcttcttttt cctacagctc 1020
ctgggcaacg tgctggttgt tgtgctgtct catcattttg gcaaagtcga cgacgaacgc 1080
gttaacgtta ctggccgaag ccgcttggaa taaggccggt gtgcgtttgt ctatatgtga 1140
ttttccacca tattgccgtc ttttggcaat gtgagggccc ggaaacctgg ccctgtcttc 1200
ttgacgagca ttcctagggg tctttcccct ctcgccaaag gaatgcaagg tctgttgaat 1260
gtcgtgaagg aagcagttcc tctggaagct tcttgaagac aaacaacgtc tgtagcgacc 1320
ctttgcaggc agcggaaccc cccacctggc gacaggtgcc tctgcggcca aaagccacgt 1380
gtataagata cacctgcaaa ggcggcacaa ccccagtgcc acgttgtgag ttggatagtt 1440
gtggaaagag tcaaatggct ctcctcaagc gtattcaaca aggggctgaa ggatgcccag 1500
aaggtacccc attgtatggg atctgatctg gggcctcggt gcacatgctt tacatgtgtt 1560
tagtcgaggt taaaaaaacg tctaggcccc ccgaaccacg gggacgtggt tttcctttga 1620
aaaacacgat gataatcgat ggcaatccta gcgtgaaggc tggtaggatt ttatccccgc 1680

```
tgccatcatg gttcgaccat tgaactgcat cgtcgccgtg tcccaaaata tggggattgg   1740
caagaacgga gacctaccct ggcctccgct caggaacgag ttcaagtact tccaaagaat   1800
gaccacaacc tcttcagtgg aaggtaaaca gaatctggtg attatgggta ggaaaacctg   1860
gttctccatt cctgagaaga atcgaccttt aaaggacaga attaatatag ttctcagtag   1920
agaactcaaa gaaccaccac gaggagctca ttttcttgcc aaaagtttgg atgatgcctt   1980
aagacttatt gaacaaccgg aattggcaag taaagtagac atggtttgga tagtcggagg   2040
cagttctgtt taccaggaag ccatgaatca accaggccac ctcagactct ttgtgacaag   2100
gatcatgcag gaatttgaaa gtgacacgtt tttcccagaa attgatttgg ggaaatataa   2160
acttctccca gaatacccag gcgtcctctc tgaggtccag gaggaaaaag gcatcaagta   2220
taagtttgaa gtctacgaga agaaagacta acaggaagat gctttcaagt tctctgctcc   2280
cctcctaaag ctatgcattt ttataagacc atgggacttt tgctggcttt agatcctcga   2340
gaatgaatgc aattgttgtt gttaacttgt ttattgcagc ttataatggt tacaaataaa   2400
gcaatagcat cacaaatttc acaaataaag catttttttc actgcattct agttgtggtt   2460
tgtccaaact catcaatgta tcttatcatg tctggataag cttggcactg gccgtcgttt   2520
tacaacgtcg tgactgggaa aaccctggcg ttacccaact taatcgcctt gcagcacatc   2580
ccccttcgc cagctggcgt aatagcgaag aggcccgcac cgatcgccct tcccaacagt   2640
tgcgcagcct gaatggcgaa tggcgcctga tgcggtattt tctccttacg catctgtgcg   2700
gtatttcaca ccgcatatgg tgcactctca gtacaatctg ctctgatgcc gcatagttaa   2760
gccagccccg acacccgcca acacccgctg acgcgccctg acgggcttgt ctgctcccgg   2820
catccgctta cagacaagct gtgaccgtct ccgggagctg catgtgtcag aggttttcac   2880
cgtcatcacc gaaacgcgcg agacgaaagg gcctcgtgat acgcctattt ttataggtta   2940
atgtcatgat aataatggtt tcttagacgt caggtggcac ttttcgggga aatgtgcgcg   3000
gaacccctat ttgtttattt ttctaaatac attcaaatat gtatccgctc atgagacaat   3060
aaccctgata aatgcttcaa taatattgaa aaaggaagag tatgagtatt caacatttcc   3120
gtgtcgccct tattcccttt tttgcggcat tttgccttcc tgtttttgct cacccagaaa   3180
cgctggtgaa agtaaaagat gctgaagatc agttgggtgc acgagtgggt tacatcgaac   3240
tggatctcaa cagcggtaag atccttgaga gttttcgccc cgaagaacgt tttccaatga   3300
tgagcacttt taaagttctg ctatgtggcg cggtattatc ccgtattgac gccgggcaag   3360
agcaactcgg tcgccgcata cactattctc agaatgactt ggttgagtac tcaccagtca   3420
cagaaaagca tcttacggat ggcatgacag taagagaatt atgcagtgct gccataacca   3480
tgagtgataa cactgcggcc aacttacttc tgacaacgat cggaggaccg aaggagctaa   3540
ccgctttttt gcacaacatg ggggatcatg taactcgcct tgatcgttgg gaaccggagc   3600
tgaatgaagc cataccaaac gacgagcgtg acaccacgat gcctgtagca atggcaacaa   3660
cgttgcgcaa actattaact ggcgaactac ttactctagc ttcccggcaa caattaatag   3720
actggatgga ggcggataaa gttgcaggac cacttctgcg ctcggccctt ccggctggct   3780
ggtttattgc tgataaatct ggagccggtg agcgtgggtc tcgcggtatc attgcagcac   3840
tggggccaga tggtaagccc tcccgtatcg tagttatcta cacgacgggg agtcaggcaa   3900
ctatggatga acgaaataga cagatcgctg agataggtgc ctcactgatt aagcattggt   3960
aactgtcaga ccaagtttac tcatatatac tttagattga tttaaaactt catttttaat   4020
```

ttaaaaggat ctaggtgaag atcctttttg ataatctcat gaccaaaatc ccttaacgtg 4080
agttttcgtt ccactgagcg tcagaccccg tagaaaagat caaaggatct tcttgagatc 4140 cttttttttct gcgcgtaatc tgctgcttgc aaacaaaaaa accaccgcta ccagcggtgg 4200
tttgtttgcc ggatcaagag ctaccaactc tttttccgaa ggtaactggc ttcagcagag 4260
cgcagatacc aaatactgtc cttctagtgt agccgtagtt aggccaccac ttcaagaact 4320
ctgtagcacc gcctacatac ctcgctctgc taatcctgtt accagtggct gctgccagtg 4380
gcgataagtc gtgtcttacc gggttggact caagacgata gttaccggat aaggcgcagc 4440
ggtcgggctg aacggggggt tcgtgcacac agcccagctt ggagcgaacg acctacaccg 4500
aactgagata cctacagcgt gagctatgag aaagcgccac gcttcccgaa gggagaaagg 4560
cggacaggta tccggtaagc ggcagggtcg gaacaggaga gcgcacgagg gagcttccag 4620
ggggaaacgc ctggtatctt tatagtcctg tcgggtttcg ccacctctga cttgagcgtc 4680
gatttttgtg atgctcgtca ggggggcgga gcctatggaa aaacgccagc aacgcggcct 4740
ttttacggtt cctggccttt tgctggcctt ttgctcacat gttctttcct gcgttatccc 4800
ctgattctgt ggataaccgt attaccgcct ttgagtgagc tgataccgct cgccgcagcc 4860
gaacgaccga gcgcagcgag tcagtgagcg aggaagcgga agagcgccca atacgcaaac 4920
cgcctctccc cgcgcgttgg ccgattcatt aatgcagctg gcacgacagg tttcccgact 4980
ggaaagcggg cagtgagcgc aacgcaatta atgtgagtta gctcactcat taggcacccc 5040
aggctttaca ctttatgctt ccggctcgta tgttgtgtgg aattgtgagc ggataacaat 5100
ttcacacagg aaacagctat gaccatgatt acgaattcag acatgataag atacattgat 5160
gagtttggac aaaccacaac tagaatgcag tgaaaaaaat gctttatttg tgaaatttgt 5220
gatgctattg ctttatttgt aaccattata agctgcaata aacaagttaa caacaacaat 5280
tgcattcatt gatatcggtg ctagttaact agaccggttt tgatctgacg gttcactaaa 5340
cgagctctgc ttatatagac ctcccaccgt acacgcctac cgcccatttg cgtcaacggg 5400
gcggggttat tacgacattt tggaaagtcc cgttgatttt ggtgccaaaa caaactccca 5460
ttgacgtcaa tggggtggag acttggaaat ccccgtgagt caaaccgcta tccacgccca 5520
ttggtgtact gccaaaaccg catcaccatg gtaatagcga tgactaatac gtagatgtac 5580
tgccaagtag gaaagtcccg taaggtcatg tactgggcat aatgccaggc gggccattta 5640
ccgtcattga cgtcaatagg gggcggactt ggcatatgat acacttgatg tactgccaag 5700
tgggcagttt accgtaaata ctccacccat tgacgtcaat ggaaagtccc tattggcgtt 5760
actatgggaa catacgtcat tattgacgtc aatgggcggg ggtcgttggg cggtcagcca 5820
ggcgggccat ttaccgtaag ttatgtaacg cggaactcca tatatgggct atgaactaat 5880
gaccccgtaa ttgattacta ttaataacta gtcaataatc aatgccaaca tggcggtcat 5940
attggacatg agccaatata aatgtacata ttatgatata gatacaacgt atgcaatggc 6000
caatagccaa tattgattta tgctatataa ccaatgaata atatggctaa tggccaatat 6060
tgag 6064

<210> SEQ ID NO 8
<211> LENGTH: 6292
<212> TYPE: DNA
<213> ORGANISM: Artificial Sequence
<220> FEATURE:
<223> OTHER INFORMATION: Synthetic oligonucleotide

<400> SEQUENCE: 8

```
cgatggcaat cctagcgtga aggctggtag gattttatcc ccgctgccat catggttcga     60
ccattgaact gcatcgtcgc cgtgtcccaa aatatgggga ttggcaagaa cggagaccta    120
ccctggcctc cgctcaggaa cgagttcaag tacttccaaa gaatgaccac aacctcttca    180
gtggaaggta aacagaatct ggtgattatg ggtaggaaaa cctggttctc cattcctgag    240
aagaatcgac ctttaaagga cagaattaat atagttctca gtagagaact caaagaacca    300
ccacgaggag ctcattttct tgccaaaagt ttggatgatg ccttaagact tattgaacaa    360
ccggaattgg caagtaaagt agacatggtt tggatagtcg gaggcagttc tgtttaccag    420
gaagccatga atcaaccagg ccacctcaga ctctttgtga caaggatcat gcaggaattt    480
gaaagtgaca cgtttttccc agaaattgat ttggggaaat ataaacttct cccagaatac    540
ccaggcgtcc tctctgaggt ccaggaggaa aaaggcatca agtataagtt tgaagtctac    600
gagaagaaag actaacagga agatgctttc aagttctctg ctcccctcct aaagctatgc    660
atttttataa gaccatggga cttttgctgg ctttagatcc tcgagaatga atgcaattgt    720
tgttgttaac ttgtttattg cagcttataa tggttacaaa taaagcaata gcatcacaaa    780
tttcacaaat aaagcatttt tttcactgca ttctagttgt ggtttgtcca aactcatcaa    840
tgtatcttat catgtctgga taagcttggc actggccgtc gttttacaac gtcgtgactg    900
ggaaaaccct ggcgttaccc aacttaatcg ccttgcagca catccccctt tcgccagctg    960
gcgtaatagc gaagaggccc gcaccgatcg cccttcccaa cagttgcgca gcctgaatgg   1020
cgaatggcgc ctgatgcggt attttctcct tacgcatctg tgcggtattt cacaccgcat   1080
atggtgcact ctcagtacaa tctgctctga tgccgcatag ttaagccagc cccgacaccc   1140
gccaacaccc gctgacgcgc cctgacgggc ttgtctgctc ccggcatccg cttacagaca   1200
agctgtgacc gtctccggga gctgcatgtg tcagaggttt tcaccgtcat caccgaaacg   1260
cgcgagacga aagggcctcg tgatacgcct atttttatag gttaatgtca tgataataat   1320
ggtttcttag acgtcaggtg gcacttttcg gggaaatgtg cgcggaaccc ctatttgttt   1380
atttttctaa atacattcaa atatgtatcc gctcatgaga caataaccct gataaatgct   1440
tcaataatat tgaaaaagga agagtatgag tattcaacat ttccgtgtcg cccttattcc   1500
cttttttgcg gcattttgcc ttcctgtttt tgctcaccca gaaacgctgg tgaaagtaaa   1560
agatgctgaa gatcagttgg gtgcacgagt gggttacatc gaactggatc tcaacagcgg   1620
taagatcctt gagagttttc gccccgaaga acgttttcca atgatgagca cttttaaagt   1680
tctgctatgt ggcgcggtat tatcccgtat tgacgccggg caagagcaac tcggtcgccg   1740
catacactat tctcagaatg acttggttga gtactcacca gtcacagaaa agcatcttac   1800
ggatggcatg acagtaagag aattatgcag tgctgccata accatgagtg ataacactgc   1860
ggccaactta cttctgacaa cgatcggagg accgaaggag ctaaccgctt ttttgcacaa   1920
catgggggat catgtaactc gccttgatcg ttgggaaccg gagctgaatg aagccatacc   1980
aaacgacgag cgtgacacca cgatgcctgt agcaatggca acaacgttgc gcaaactatt   2040
aactggcgaa ctacttactc tagcttcccg gcaacaatta atagactgga tggaggcgga   2100
taaagttgca ggaccacttc tgcgctcggc ccttccggct ggctggttta ttgctgataa   2160
atctggagcc ggtgagcgtg ggtctcgcgg tatcattgca gcactggggc cagatggtaa   2220
gccctcccgt atcgtagtta tctacacgac ggggagtcag gcaactatgg atgaacgaaa   2280
tagacagatc gctgagatag gtgcctcact gattaagcat tggtaactgt cagaccaagt   2340
```

```
ttactcatat atactttaga ttgatttaaa acttcatttt taatttaaaa ggatctaggt   2400
gaagatcctt tttgataatc tcatgaccaa aatcccttaa cgtgagtttt cgttccactg   2460
agcgtcagac cccgtagaaa agatcaaagg atcttcttga gatccttttt ttctgcgcgt   2520
aatctgctgc ttgcaaacaa aaaaaccacc gctaccagcg gtggtttgtt tgccggatca   2580
agagctacca actctttttc cgaaggtaac tggcttcagc agagcgcaga taccaaatac   2640
tgtccttcta gtgtagccgt agttaggcca ccacttcaag aactctgtag caccgcctac   2700
atacctcgct ctgctaatcc tgttaccagt ggctgctgcc agtggcgata agtcgtgtct   2760
taccgggttg gactcaagac gatagttacc ggataaggcg cagcggtcgg gctgaacggg   2820
gggttcgtgc acacagccca gcttggagcg aacgacctac accgaactga gatacctaca   2880
gcgtgagcta tgagaaagcg ccacgcttcc cgaagggaga aaggcggaca ggtatccggt   2940
aagcggcagg gtcggaacag gagagcgcac gagggagctt ccagggggaa acgcctggta   3000
tctttatagt cctgtcgggt ttcgccacct ctgacttgag cgtcgatttt tgtgatgctc   3060
gtcagggggg cggagcctat ggaaaaacgc cagcaacgcg gcctttttac ggttcctggc   3120
cttttgctgg ccttttgctc acatgttctt tcctgcgtta tcccctgatt ctgtggataa   3180
ccgtattacc gcctttgagt gagctgatac cgctcgccgc agccgaacga ccgagcgcag   3240
cgagtcagtg agcgaggaag cggaagagcg cccaatacgc aaaccgcctc tccccgcgcg   3300
ttggccgatt cattaatgca gctggcacga caggtttccc gactggaaag cgggcagtga   3360
gcgcaacgca attaatgtga gttagctcac tcattaggca ccccaggctt tacactttat   3420
gcttccggct cgtatgttgt gtggaattgt gagcggataa caatttcaca caggaaacag   3480
ctatgaccat gattacgaat tccagctgtg gaatgtgtgt cagttagggt gtggaaagtc   3540
cccaggctcc ccagcaggca gaagtatgca aagcatgcat ctcaattagt cagcaaccag   3600
gtgtggaaag tccccaggct ccccagcagg cagaagtatg caaagcatgc atctcaatta   3660
gtcagcaacc atagtcccgc ccctaactcc gcccatcccg cccctaactc cgcccagttc   3720
cgcccattct ccgccccatg gctgactaat tttttttatt tatgcagagg ccgaggccgc   3780
ctcggcctct gagctattcc agaagtagtg aggaggcttt tttggaggcc taggcttttg   3840
caaaaagcga tcctgagaac ttcagggtga gtttggggac ccttgattgt tctttctttt   3900
tcgctattgt aaaattcatg ttatatggag ggggcaaagt tttcagggtg ttgtttagaa   3960
tgggaagatg tcccttgtat caccatggac cctcatgata attttgtttc tttcactttc   4020
tactctgttg acaaccattg tctcctctta ttttcttttc attttctgta actttttcgt   4080
taaactttag cttgcatttg taacgaattt ttaaattcac ttttgtttat ttgtcagatt   4140
gtaagtactt tctctaatca cttttttttc aaggcaatca gggtatatta tattgtactt   4200
cagcacagtt ttagagaaca attgttataa ttaaatgata aggtagaata tttctgcata   4260
taaattctgg ctggcgtgga aatattctta ttggtagaaa caactacatc ctggtcatca   4320
tcctgccttt ctctttatgg ttacaatgat atacactgtt tgagatgagg ataaaatact   4380
ctgagtccaa accgggcccc tctgctaacc atgttcatgc cttcttcttt ttcctacagc   4440
tcctgggcaa cgtgctggtt gttgtgctgt ctcatcattt tggcaaaacc ggttagtgat   4500
atcaatgaat gcaattgttg ttgttaactt gtttattgca gcttataatg gttacaaata   4560
aagcaatagc atcacaaatt tcacaaataa agcatttttt tcactgcatt ctagttgtgg   4620
tttgtccaaa ctcatcaatg tatcttatca tgtctggatc ccgggcgcag caccatggcc   4680
tgaaataacc tctgaaagag gaacttggtt aggtaccttc tgaggcggaa agaaccagct   4740
```

-continued

```
gtggaatgtg tgtcagttag ggtgtggaaa gtccccaggc tccccagcag gcagaagtat   4800
gcaaagcatg catctcaatt agtcagcaac caggtgtgga aagtccccag gctccccagc   4860
aggcagaagt atgcaaagca tgcatctcaa ttagtcagca accatagtcc cgcccctaac   4920
tccgcccatc ccgcccctaa ctccgcccag ttccgcccat tctccgcccc atggctgact   4980
aattttttt atttatgcag aggccgaggc cgcctcggcc tctgagctat tccagaagta   5040
gtgaggaggc ttttttggag gcctaggctt ttgcaaaaag ctgatcctga gaacttcagg   5100
gtgagtttgg ggacccttga ttgttctttc tttttcgcta ttgtaaaatt catgttatat   5160
ggagggggca aagttttcag ggtgttgttt agaatgggaa gatgtccctt gtatcaccat   5220
ggaccctcat gataattttg tttctttcac tttctactct gttgacaacc attgtctcct   5280
cttattttct tttcattttc tgtaactttt tcgttaaact ttagcttgca tttgtaacga   5340
atttttaaat tcacttttgt ttatttgtca gattgtaagt actttctcta atcacttttt   5400
tttcaaggca atcagggtat attatattgt acttcagcac agttttagag aacaattgtt   5460
ataattaaat gataaggtag aatatttctg catataaatt ctggctggcg tggaaatatt   5520
cttattggta gaaacaacta catcctggtc atcatcctgc ctttctcttt atggttacaa   5580
tgatatacac tgtttgagat gaggataaaa tactctgagt ccaaaccggg cccctctgct   5640
aaccatgttc atgccttctt ctttttccta cagctcctgg gcaacgtgct ggttgttgtg   5700
ctgtctcatc attttggcaa agtcgacgac gaacgcgtta acgttactgg ccgaagccgc   5760
ttggaataag gccggtgtgc gtttgtctat atgtgatttt ccaccatatt gccgtctttt   5820
ggcaatgtga gggcccggaa acctggccct gtcttcttga cgagcattcc taggggtctt   5880
tcccctctcg ccaaaggaat gcaaggtctg ttgaatgtcg tgaaggaagc agttcctctg   5940
gaagcttctt gaagacaaac aacgtctgta gcgacccttt gcaggcagcg gaacccccca   6000
cctggcgaca ggtgcctctg cggccaaaag ccacgtgtat aagatacacc tgcaaaggcg   6060
gcacaacccc agtgccacgt tgtgagttgg atagttgtgg aaagagtcaa atggctctcc   6120
tcaagcgtat tcaacaaggg gctgaaggat gcccagaagg taccccattg tatgggatct   6180
gatctggggc ctcggtgcac atgctttaca tgtgtttagt cgaggttaaa aaaacgtcta   6240
ggccccccga accacgggga cgtggttttc ctttgaaaaa cacgatgata at           6292
```